United States Patent
Shim et al.

(10) Patent No.: US 10,556,567 B2
(45) Date of Patent: Feb. 11, 2020

(54) MOBILE TERMINAL AND CONTROL METHOD THEREOF

(71) Applicant: LG ELECTRONICS INC., Seoul (KR)

(72) Inventors: Hongjo Shim, Seoul (KR); Hyunok Lee, Seoul (KR); Hyunwoo Kim, Seoul (KR); Youngho Sohn, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 131 days.

(21) Appl. No.: 15/641,772

(22) Filed: Jul. 5, 2017

(65) Prior Publication Data

US 2018/0072267 A1     Mar. 15, 2018

(30) Foreign Application Priority Data

Sep. 13, 2016  (KR) .......................... 10-2016-0118288

(51) Int. Cl.
*B60R 25/24*     (2013.01)
*G07C 9/00*      (2006.01)
*G08C 17/02*     (2006.01)
*G06F 3/0488*    (2013.01)

(52) U.S. Cl.
CPC .......... *B60R 25/24* (2013.01); *G07C 9/00309* (2013.01); *G08C 17/02* (2013.01); *B60R 2325/101* (2013.01); *G06F 3/04883* (2013.01); *G07C 2009/00793* (2013.01); *G07C 2009/00984* (2013.01)

(58) Field of Classification Search
None
See application file for complete search history.

(56) References Cited

U.S. PATENT DOCUMENTS

| | | | | |
|---|---|---|---|---|
| 7,301,442 | B2* | 11/2007 | Kolpasky | B60R 25/257 307/10.2 |
| 9,118,750 | B2* | 8/2015 | Vossoughi | B60R 11/02 |
| 9,505,413 | B2* | 11/2016 | Laine | G08G 1/165 |
| 2003/0071791 | A1* | 4/2003 | Hanson | G06F 1/1601 345/169 |
| 2014/0239065 | A1 | 8/2014 | Zhou et al. | |
| 2015/0223355 | A1 | 8/2015 | Fleck et al. | |
| 2016/0063777 | A1* | 3/2016 | Wooley | A61B 5/00 340/5.61 |

FOREIGN PATENT DOCUMENTS

| | | |
|---|---|---|
| EP | 0960995 A2 | 12/1999 |
| EP | 1065791 A2 | 1/2001 |
| WO | WO 2016/060342 A1 | 4/2016 |

* cited by examiner

*Primary Examiner* — Carlos Garcia
(74) *Attorney, Agent, or Firm* — Birch, Stewart, Kolasch & Birch, LLP

(57) ABSTRACT

A watch type mobile terminal including a wrist band; a main system including a circuit board for operating the watch type mobile terminal; a main frame connected to the wrist band and encasing the main system; a fob detachably connected to the main system; and a display detachably connected to the fob.

10 Claims, 11 Drawing Sheets

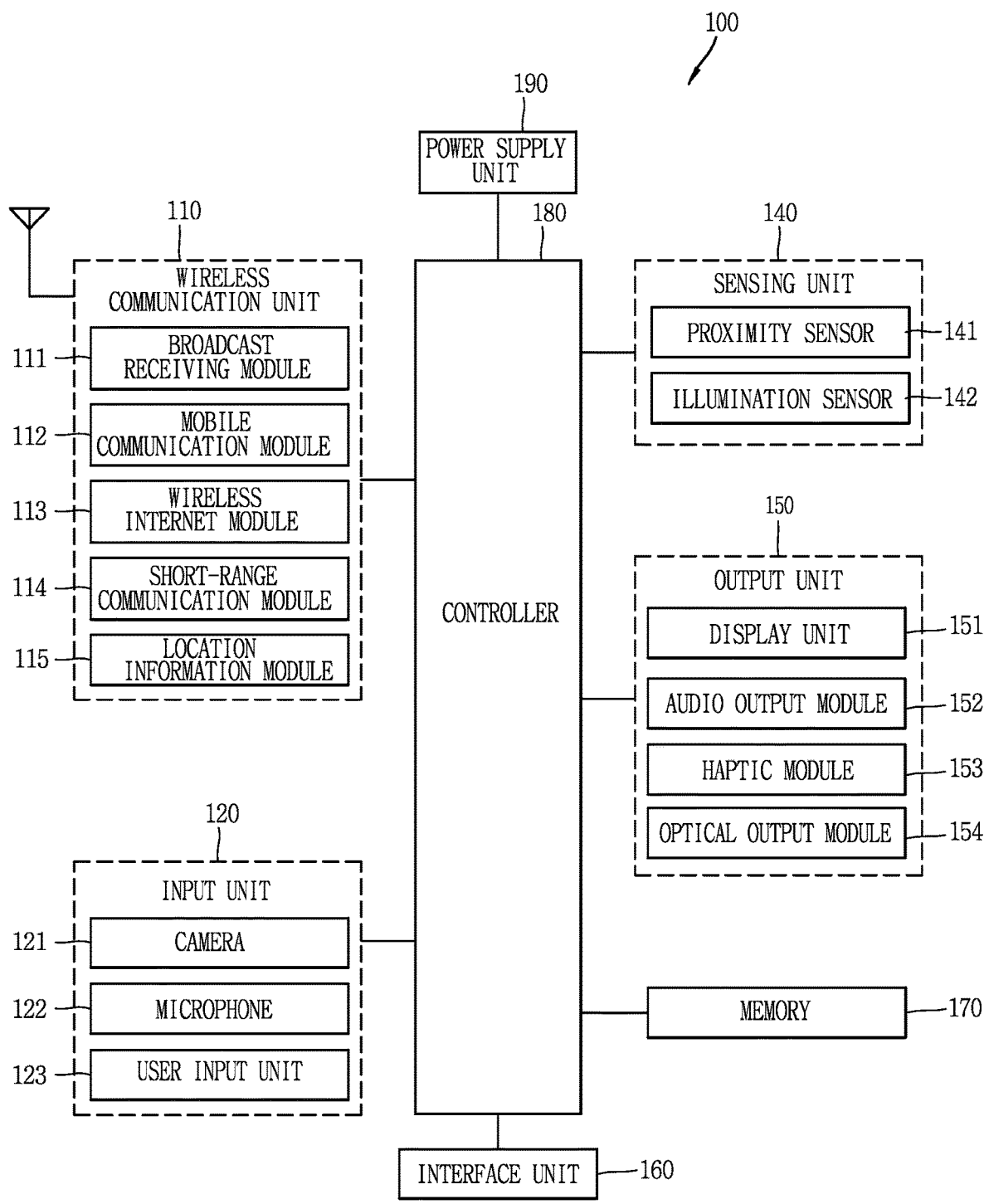

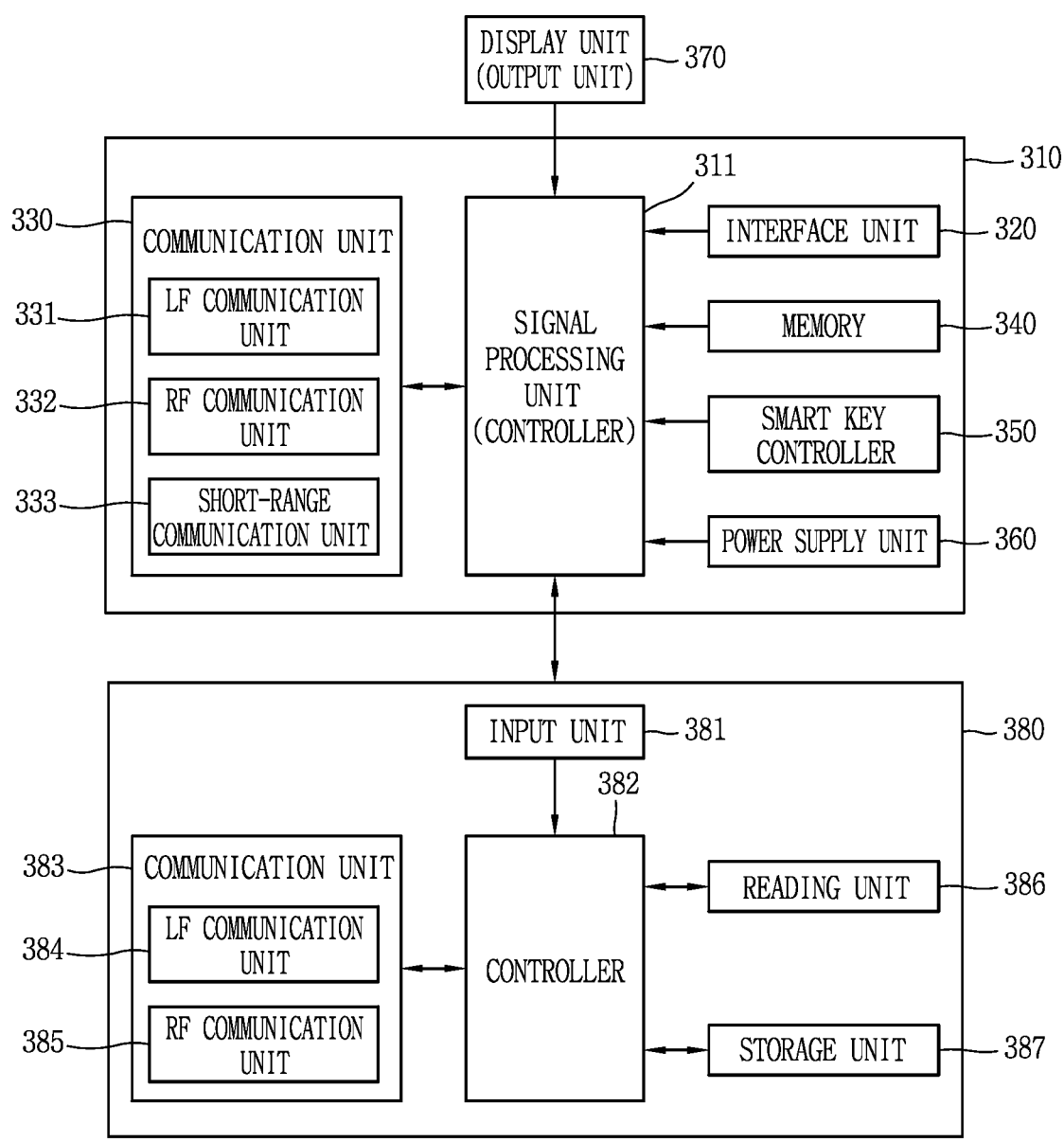

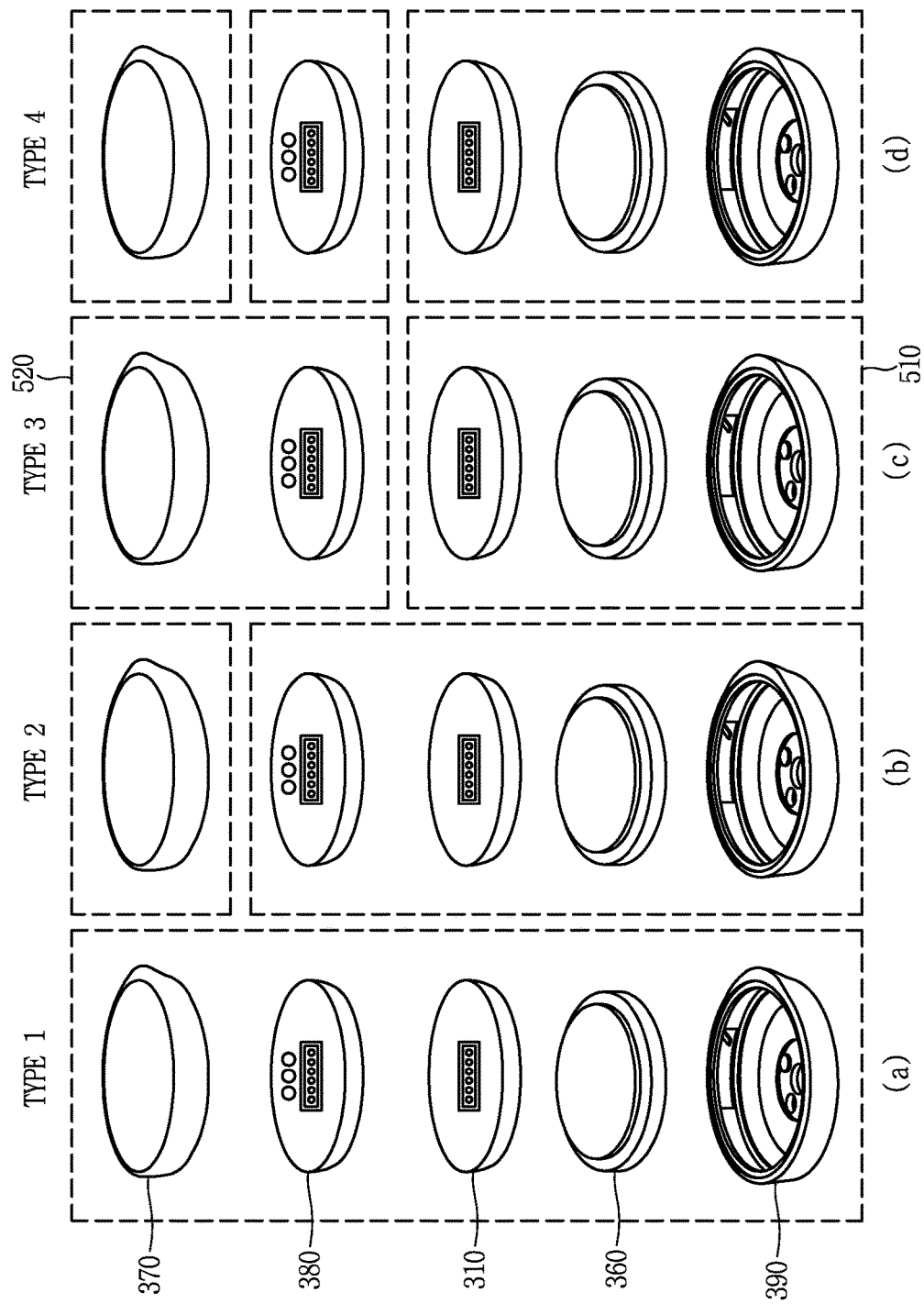

(a)

(b)

MOBILE TERMINAL AND CONTROL METHOD THEREOF

CROSS-REFERENCE TO RELATED APPLICATION

Pursuant to 35 U.S.C. § 119(a), this application claims the benefit of earlier filing date and right of priority to Korean Application No. 10-2016-0118288, filed on Sep. 13, 2016, the contents of which is incorporated by reference herein in its entirety.

BACKGROUND OF THE INVENTION

1. Field of the Invention

The present disclosure relates to a mobile terminal wearable on a user's wrist and a control method thereof.

2. Background of the Invention

Terminals may be generally classified as mobile/portable terminals or stationary terminals. Mobile terminals may also be classified as handheld terminals or vehicle mounted terminals.

Mobile terminals have become increasingly more functional. Examples of such functions include data and voice communications, capturing images and video via a camera, recording audio, playing music files via a speaker system, and displaying images and video on a display. More recently, mobile terminals have been configured to receive broadcast and multicast signals which permit viewing of content such as videos and television programs.

As functions of the terminal become more diversified, the terminal can support more complicated functions such as capturing images or video, reproducing music or video files, playing games, receiving broadcast signals, and the like. By comprehensively and collectively implementing such functions, the mobile terminal may be embodied in the form of a multimedia player or a device.

Efforts are ongoing to support and increase the functionality of mobile terminals. Such efforts include software and hardware improvements, as well as changes and improvements in the structural components.

Recently, a remote keyless entry (RKE) for opening and closing a door is provided in vehicles. In particular, RKE is a function allowing a user to open or close a door of a vehicle using a lock button or an unlock button. In addition, a driver may carry packages in both hands or hold their baby in many situations. However, it is difficult or cumbersome for the driver to press the lock button or the unlock button of the RKE. Thus, a technique of controlling a vehicle using a mobile terminal has been actively developed.

SUMMARY OF THE INVENTION

Therefore, an aspect of the detailed description is to provide a mobile terminal configured such that a portion of a main body thereof is detachable.

Another aspect of the detailed description is to provide a mobile terminal capable of controlling an external device in an optimized manner using a separated main body thereof, and a control method thereof.

To achieve these and other advantages and in accordance with the purpose of this specification, as embodied and broadly described herein, a mobile terminal includes: a band worn on a user's wrist to surround the wrist; a main frame connected to the band; a main system provided in the main frame; a FOB module provided to be detachably attached to the main system; and a display unit provided to be detachably attached to the FOB module.

To achieve these and other advantages and in accordance with the purpose of this specification, as embodied and broadly described herein, a control method of a mobile terminal includes: sensing that a display unit is separated from a FOB module; sensing information through a sensing unit provided in a watch type mobile terminal in a state in which the separated display unit is attached to the external terminal; and displaying information related to the sensed information on at least one of the display unit and a touch screen of the external terminal.

The mobile terminal and the control method thereof according to embodiments of the present disclosure have the following advantages.

In the present disclosure, it is possible to separate at least one of the main system, the FOB module, and the display unit, and a novel watch type mobile terminal configured to allow the separated component to be attached to an external device are provided.

Also, in the present disclosure, when the display unit is attached to an external device, at least one of information related to the external device to which the display unit is attached and information related to the watch type mobile terminal can be output on the display unit, whereby a watch type mobile terminal capable of expanding a display space of the external device is provided.

An additional scope of applicability of the present invention shall become obvious from the detailed description in the following. It is to be understood that both the foregoing general description and the following detailed description of the preferred embodiments of the present invention are exemplary and explanatory and are intended to provide further explanation of the invention as claimed.

Further scope of applicability of the present application will become more apparent from the detailed description given hereinafter. However, it should be understood that the detailed description and specific examples, while indicating preferred embodiments of the invention, are given by way of illustration only, since various changes and modifications within the scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings:

FIG. 1A is a block diagram of a mobile terminal according to an embodiment of the present disclosure.

FIGS. 3A, 3B, and 3C are conceptual views illustrating a watch type mobile terminal according to an embodiment of the present disclosure.

DETAILED DESCRIPTION OF THE INVENTION

Figure 1B:
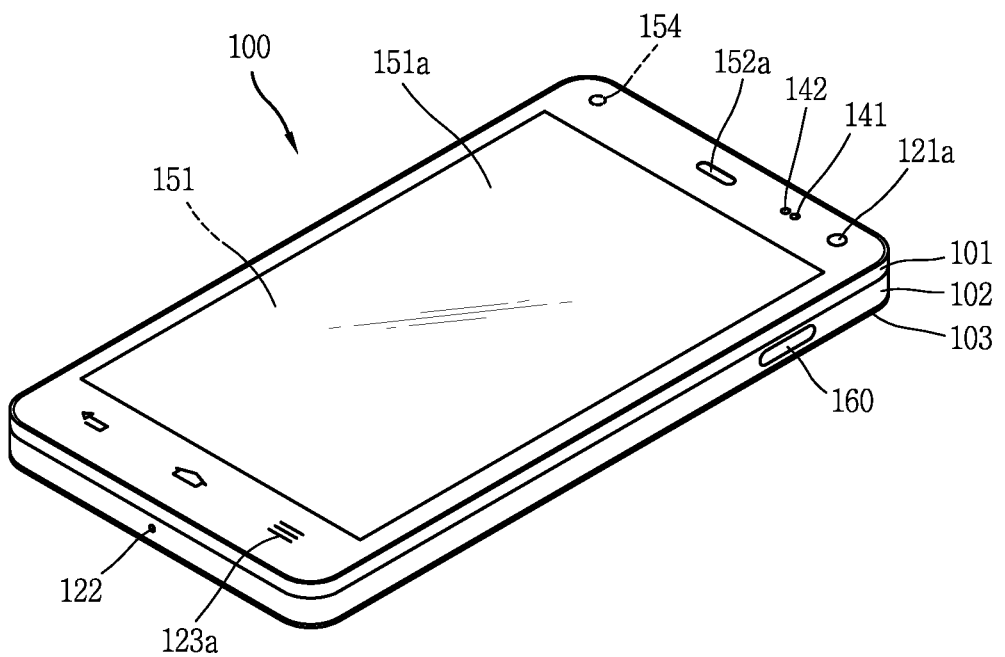
FIGS. 1B and 1C are conceptual views of one example of the mobile terminal, viewed from different directions.

Description will now be given in detail of the exemplary embodiments, with reference to the accompanying drawings. For the sake of brief description with reference to the drawings, the same or equivalent components will be provided with the same reference numbers, and description thereof will not be repeated. A suffix "module" or "unit" used for constituent elements disclosed in the following description is merely intended for easy description of the specification, and the suffix itself does not give any special meaning or function. In describing the present invention, if a detailed explanation for a related known function or construction is considered to unnecessarily divert the gist of the present disclosure, such explanation has been omitted but would be understood by those skilled in the art. The accompanying drawings are used to help easily understood the technical idea of the present invention and it should be understood that the idea of the present disclosure is not limited by the accompanying drawings. In the following description, explanations will be made in order in the clockwise direction based on the drawing in a right upper side.

Although the terms first, second, etc. may be used herein to describe various elements, these elements should not be limited by these terms. These terms are generally only used to distinguish one element from another. When an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1C:
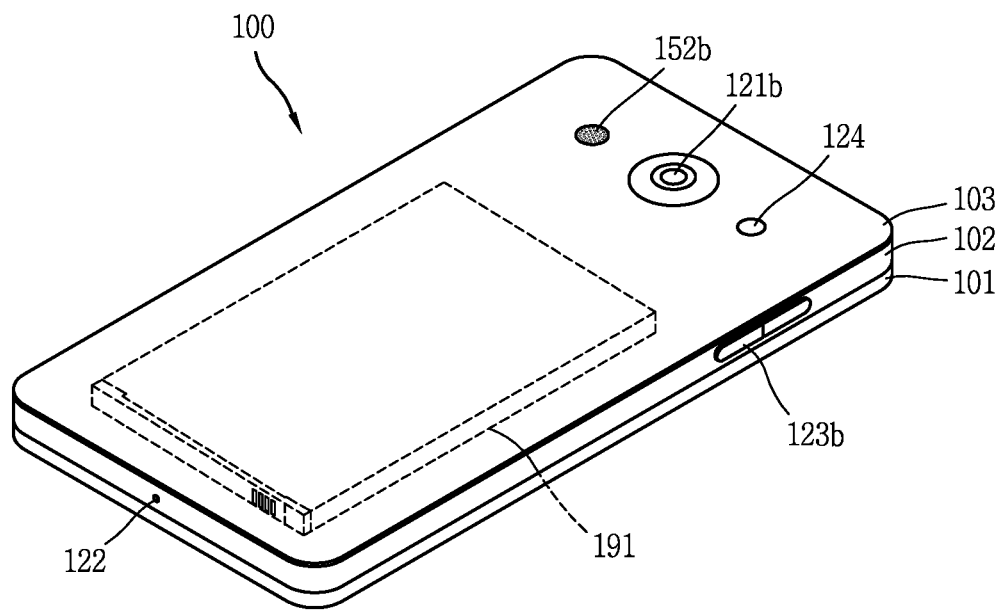

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. Implementing all of the illustrated components is not a requirement, and that greater or fewer components may alternatively be implemented.

Referring now to FIG. 1A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 can provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least some of the above components may operate in a cooperating manner, so as to implement an operation or a control method of a glass type terminal according to various embodiments to be explained later. The operation or the control method of the glass type terminal may be implemented on the glass type terminal by driving at least one application program stored in the memory 170.

Referring still to FIG. 1A, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which can exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. Further, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sensing unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this instance, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 can sense which region of the display unit 151 has been touched. Further, the touch controller may be a component separate from the controller 180, the controller 180, and combinations thereof In some embodiments, the controller 180 can execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor. Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented so the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 can typically control the general operations of the mobile terminal 100. For example, the controller 180 can set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance. Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151*a* of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121*b* or an audio output module 152*b*.

The cases 101, 102, 103 may be formed by injection-molding synthetic resin or may be formed of a metal, for example, stainless steel (STS), aluminum (Al), titanium (Ti), or the like. As an alternative to the example in which the plurality of cases form an inner space for accommodating components, the mobile terminal 100 may be configured such that one case forms the inner space. In this example, a mobile terminal 100 having a uni-body is formed so synthetic resin or metal extends from a side surface to a rear surface.

If desired, the mobile terminal 100 may include a waterproofing unit for preventing introduction of water into the terminal body. For example, the waterproofing unit may include a waterproofing member which is located between the window 151*a* and the front case 101, between the front case 101 and the rear case 102, or between the rear case 102 and the rear cover 103, to hermetically seal an inner space when those cases are coupled.

The mobile terminal 100 may include the display unit 151, the first audio output module 152*a*, the second audio output module 152*b*, the proximity sensor 141, the illumination sensor 142, the optical output module 154, the first camera 121*a*, the second camera 121*b*, the first manipulation unit 123*a*, the second manipulation unit 123*b*, the microphone 122, the interface unit 160, etc.

Hereinafter, the mobile terminal 100 will be explained with reference to FIGS. 1B and 1C. The display unit 151, the first audio output module 152*a*, the proximity sensor 141, the illumination sensor 142, the optical output module 154, the first camera 121*a* and the first manipulation unit 123*a* are arranged on the front surface of the terminal body. The second manipulation unit 123*b*, the microphone 122 and the interface unit 160 are arranged on the side surfaces of the terminal body. The second audio output module 152*b* and the second camera 121*b* are arranged on the rear surface of the terminal body.

However, alternative arrangements are possible and within the teachings of the instant disclosure. Some components may be omitted or rearranged. For example, the first manipulation unit 123*a* may be located on another surface of the terminal body, and the second audio output module 152*b* may be located on the side surface of the terminal body.

The display unit 151 outputs information processed in the mobile terminal 100. For example, the display unit 151 may display information on an execution screen of an application program driven in the mobile terminal 100, or a User Interface (UI) or a Graphic User Interface (GUI) associated with such execution screen information.

The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151*a* and a display on a rear surface of the window 151*a*, or a metal wire which is patterned directly on the rear surface of the window 151*a*. Alternatively, the touch sensor may be integrally formed with the display. For example, the touch sensor may be disposed on a substrate of the display or within the display.

The display unit 151 may also form a touch screen together with the touch sensor. Further, the touch screen may serve as the user input unit 123 (see FIG. 1A). Therefore, the touch screen may replace at least some of the functions of the first manipulation unit 123*a*.

The first audio output unit 152*a* may be implemented as a receiver for transmitting a call sound to a user's ears, and the second audio output unit 152*b* may be implemented as a loud speaker for outputting each type of alarm sounds or a play sound of multimedia.

It may be configured such that the sounds generated from the first audio output module 152*a* are released along an assembly gap between the structural bodies (e.g., between the window 151*a* and the front case 101). In this instance, a hole independently formed to output audio sounds may not be seen or hidden in terms of appearance, thereby further simplifying the appearance of the mobile terminal 100.

The optical output module 154 can output a signal for indicating an event generation using light of a light source. Examples of events generated in the mobile terminal 100 may include message reception, call signal reception, a missed call, an alarm, a schedule notice, an email reception, information reception through an application, and the like. A signal output by the optical output module 154 may be implemented so the mobile terminal emits monochromatic light or light with a plurality of colors. The signal output may be terminated as the mobile terminal senses that a user has checked the generated event, for example.

The first camera 121*a* processes image data of still pictures or video acquired by an image capture device in a video capturing mode or an image capturing mode. The processed image frames may be displayed on the display unit 151, or may be stored in the memory 170.

The first and second manipulation units 123*a* and 123*b* are examples of the user input unit 123, which may be manipulated by a user to provide input to the mobile terminal 100. The first and second manipulation units 123*a* and 123*b* may also be commonly referred to as a manipulating portion, and may employ any tactile method that allows the user to perform manipulation such as touch, push, scroll, or the like. The first and second manipulation units 123*a* and 123*b* may be implemented in a user's non-tactile manner, e.g., by a proximity touch, a hovering touch, etc.

FIG. 1B illustrates the first manipulation unit 123*a* as a touch key, but possible alternatives include a mechanical key, a push key, a touch key, and combinations thereof. Input received at the first and second manipulation units 123*a* and 123*b* may be used in various ways. For example, the first manipulation unit 123*a* may be used by the user to provide an input to a menu, home key, cancel, search, or the like, and the second manipulation unit 123*b* may be used by the user to provide an input to control a volume level being output from the first or second audio output modules 152*a* or 152*b*, to switch to a touch recognition mode of the display unit 151, or the like.

As another example of the user input unit 123, a rear input unit may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152*a* or 152*b*, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123*a* in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject. As shown in FIG. 1C, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 (refer to FIG. 1A) may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

In some embodiments, another mobile terminal (which may be configured similarly to mobile terminal 100) may be a wearable device, for example, a smart watch, a smart glass or a head mounted display (HMD), which can exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the control unit 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

Figure 2:
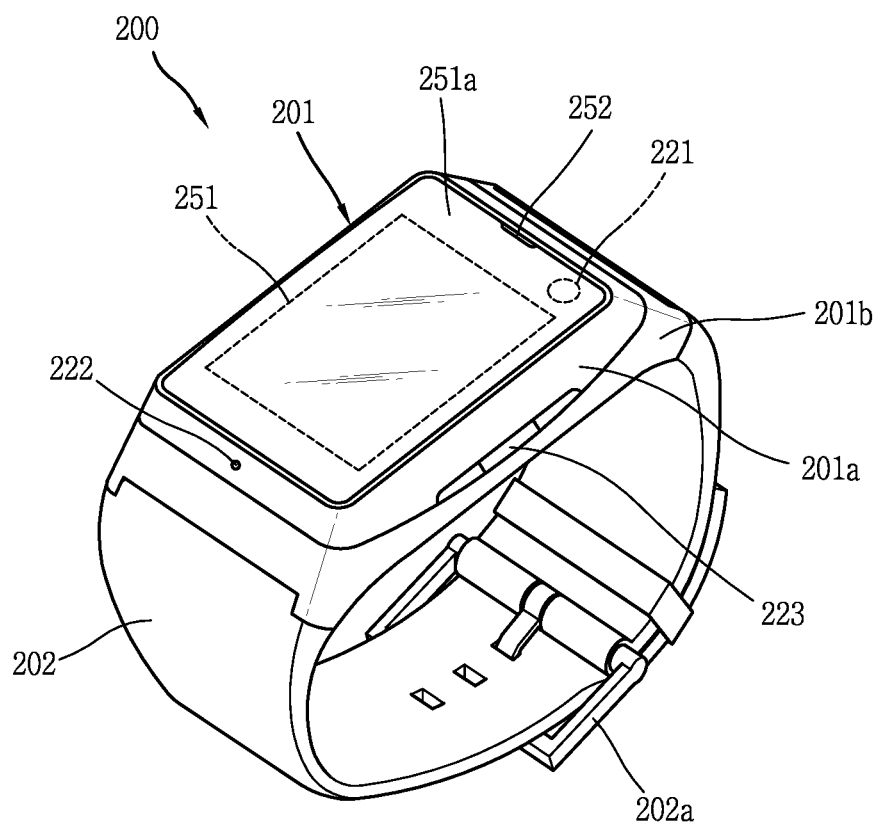
FIG. 2 is a perspective view illustrating an example of a watch type mobile terminal related to another embodiment of the present disclosure.

FIG. 2 is a perspective view illustrating one example of a watch-type wearable device 200 in accordance with another exemplary embodiment. As illustrated in FIG. 2, the watch-type wearable device 200 includes a main body 201 with a display unit 251 and a band 202 connected to the main body 201 to be wearable on a wrist. In general, wearable device 200 may be configured to include features that are the same or similar to that of the mobile terminal 100 of FIGS. 1A to 1C.

The main body 201 may include a case having a certain appearance. As illustrated, the case may include a first case 201a and a second case 201b cooperatively defining an inner space for accommodating various electronic components. Other configurations are possible. For instance, a single case may alternatively be implemented, with such a case being configured to define the inner space, thereby implementing a watch-type wearable device 200 with a uni-body.

The watch-type wearable device 200 can perform wireless communication, and an antenna for the wireless communication can be installed in the main body 201. The antenna may extend its function using the case. For example, a case including a conductive material may be electrically connected to the antenna to extend a ground area or a radiation area.

The display unit 251 is shown located at the front side of the main body 201 so that displayed information is viewable to a user. In some embodiments, the display unit 251 includes a touch sensor so that the display unit can function as a touch screen. As illustrated, window 251a is positioned on the first case 201a to form a front surface of the terminal body together with the first case 201a.

The illustrated embodiment includes audio output module 252, a camera 221, a microphone 222, and a user input unit 223 positioned on the main body 201. When the display unit 251 is implemented as a touch screen, additional function keys may be minimized or eliminated. For example, when the touch screen is implemented, the user input unit 223 may be omitted.

The band 202 is commonly worn on the user's wrist and may be made of a flexible material for facilitating wearing of the device. As one example, the band 202 may be made of fur, rubber, silicon, synthetic resin, or the like. The band 202 may also be configured to be detachable from the main body 201. Accordingly, the band 202 may be replaceable with various types of bands according to a user's preference.

In one configuration, the band 202 may be used for extending the performance of the antenna. For example, the band may include therein a ground extending portion electrically connected to the antenna to extend a ground area. The band 202 may include fastener 202a. The fastener 202a may be implemented into a buckle type, a snap-fit hook structure, a Velcro® type, or the like, and include a flexible section or material. The drawing illustrates an example that the fastener 202a is implemented using a buckle.

Hereinafter, a communication system which is operable with the mobile terminal 100 according to the present disclosure will be described. Such communication systems utilize different air interfaces and/or physical layers. Examples of such air interfaces utilized by the communication systems include Frequency Division Multiple Access (FDMA), Time Division Multiple Access (TDMA), Code Division Multiple Access (CDMA), and Universal Mobile Telecommunications System (UMTS), the Long Term Evolution (LTE) of the UMTS, the Global System for Mobile Communications (GSM), and the like.

By way of non-limiting example only, further description will relate to a CDMA communication system, but such teachings apply equally to other system types including the CDMA wireless communication system. A CDMA wireless communication system is shown having a plurality of mobile terminals 100, a plurality of base stations (BSs), base station controllers (BSCs), and a mobile switching center (MSC). The MSC is configured to interface with a conventional Public Switch Telephone Network (PSTN). The MSC is also configured to interface with the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations. The base stations may also be denoted as "cell sites." Alternatively, individual sectors of a given base station may be referred to as cell sites.

A broadcasting transmitter (BT) transmits a broadcast signal to the mobile terminals 100 operating within the system. The broadcast receiving module 111 (FIG. 1A) is typically configured inside the mobile terminal 100 to receive broadcast signals transmitted by the BT.

Global Positioning System (GPS) satellites 300 facilitate locating the position of at least one of plural mobile terminals 100. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites 300 may alternatively or additionally be configured to provide satellite DMB transmissions.

The location information module 115 is generally configured to detect, calculate, or otherwise identify a position of the mobile terminal. As an example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 can measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites.

Furthermore, the GPS module can acquire speed information in real time to calculate a current position. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology typically includes the use of a Wi-Fi module in the mobile terminal 100 and a wireless access point for communicating with the Wi-Fi module.

The Wi-Fi positioning system may include a Wi-Fi location determination server, a mobile terminal, a wireless access point (AP) connected to the mobile terminal, and a database stored with wireless AP information.

The mobile terminal connected to the wireless AP may transmit a location information request message to the Wi-Fi location determination server. The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database. The information of any wireless APs stored in the database may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like. In order to remove wireless APs provided using a mobile AP or an illegal MAC address during a location determining process, the Wi-Fi location determination server may extract only a predetermined number of wireless AP information in order of high RSSI. Then, the Wi-Fi location determination server may extract (analyze) location information of the mobile terminal 100 using at least one wireless AP information extracted from the database.

A method for extracting (analyzing) location information of the mobile terminal 100 may include a Cell-ID method, a fingerprint method, a trigonometry method, a landmark method, and the like. The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate a position of a mobile terminal based on a distance between coordinates of at least three wireless APs and the mobile terminal. In order to measure the distance between the mobile terminal and the wireless APs, signal strength may be converted into distance information, Time of Arrival (ToA), Time Difference of Arrival (TDoA), Angle of Arrival (AoA), or the like may be taken for transmitted wireless signals.

The landmark method is used to measure a position of a mobile terminal using a known landmark transmitter. In addition to these position location methods, various algorithms may be used to extract (analyze) location information of a mobile terminal. Such extracted location information may be transmitted to the mobile terminal 100 through the Wi-Fi location determination server, thereby acquiring location information of the mobile terminal 100.

The mobile terminal 100 can acquire location information by being connected to at least one wireless AP. The number of wireless APs required to acquire location information of the mobile terminal 100 may be variously changed according to a wireless communication environment within which the mobile terminal 100 is positioned.

As previously described with regard to FIG. 1A, the mobile terminal may be configured to include short-range communication techniques such as Bluetooth™, Radio Frequency Identification (RFID), Infrared Data Association (IrDA), Ultra Wideband (UWB), ZigBee, Near Field Communication (NFC), Wireless USB (Wireless Universal Serial Bus), and the like.

A typical NFC module provided at the mobile terminal supports short-range wireless communication, which is a non-contactable type of communication between mobile terminals and generally occurs within about 10 cm. The NFC module may operate in one of a card mode, a reader mode, or a P2P mode. The mobile terminal 100 may further include a security module for storing card information, in order to operate the NFC module in a card mode. The security module may be a physical medium such as Universal Integrated Circuit Card (UICC) (e.g., a Subscriber Identification Module (SIM) or Universal SIM (USIM)), a secure micro SD and a sticker, or a logical medium (e.g., embedded Secure Element (SE)) embedded in the mobile terminal. Single Wire Protocol (SWP)-based data exchange may be performed between the NFC module and the security module.

When the NFC module operates in a card mode, the mobile terminal may transmit card information on a general IC card to the outside. More specifically, if a mobile terminal having card information on a payment card (e. g, a credit card or a bus card) approaches a card reader, a short-range mobile payment may be executed. As another example, if a mobile terminal which stores card information on an entrance card approaches an entrance card reader, an entrance approval procedure may start. A card such as a credit card, a traffic card, or an entrance card may be included in the security module in the form of applet, and the security module may store card information on the card mounted therein. Card information for a payment card may include any of a card number, a remaining amount and usage history, and the like. Card information of an entrance card may include any of a user's name, a user's number (e.g., undergraduate number or staff number), an entrance history, and the like.

When the NFC module operates in a reader mode, the mobile terminal can read data from an external tag. The data received from the external tag by the mobile terminal may be coded into the NFC Data Exchange Format defined by the NFC Forum. The NFC Forum generally defines four record types. More specifically, the NFC Forum defines four Record Type Definitions (RTDs) such as smart poster, text, Uniform Resource Identifier (URI), and general control. If the data received from the external tag is a smart poster type, the controller may execute a browser (e.g., Internet browser). If the data received from the external tag is a text type, the controller may execute a text viewer. If the data received from the external tag is a URI type, the controller may execute a browser or originate a call. If the data received from the external tag is a general control type, the controller may execute a proper operation according to control content.

In some cases in which the NFC module operates in a P2P (Peer-to-Peer) mode, the mobile terminal can execute P2P communication with another mobile terminal. In this instance, Logical Link Control Protocol (LLCP) may be applied to the P2P communication. For P2P communication, connection may be generated between the mobile terminal and another mobile terminal. This connection may be categorized as a connectionless mode which ends after one packet is switched, and a connection-oriented mode in which packets are switched consecutively. For a typical P2P communication, data such as an electronic type name card, address information, a digital photo and a URL, a setup parameter for Bluetooth connection, Wi-Fi connection, etc. may be switched. The P2P mode can be effectively utilized in switching data of a small capacity, because an available distance for NFC communication is relatively short.

The GPS (Global Position System) module, the WiFi (Wireless Fidelity) module, and the NFC module described above may be applied to a watch type mobile terminal 200, and may also be applied to at least one of a main system 310, a FOB module 380, and a display 370 described hereinafter. In other words, at least one of the components described above may be included in (or applied to) the watch type mobile terminal 200 of the present disclosure.

Hereinafter, embodiments related to a control method that may be implemented in a mobile terminal configured described above will be described with reference to the accompanying drawings. The present invention may be performed in other specific ways than those set forth herein without departing from the spirit and essential characteristics of the present invention.

The present disclosure relates to a watch type mobile terminal and may include at least one component discussed above with reference to FIGS. 1A to 2. Hereinafter, a watch type mobile terminal according to an embodiment of the present disclosure will be described in detail.

Figure 3B:
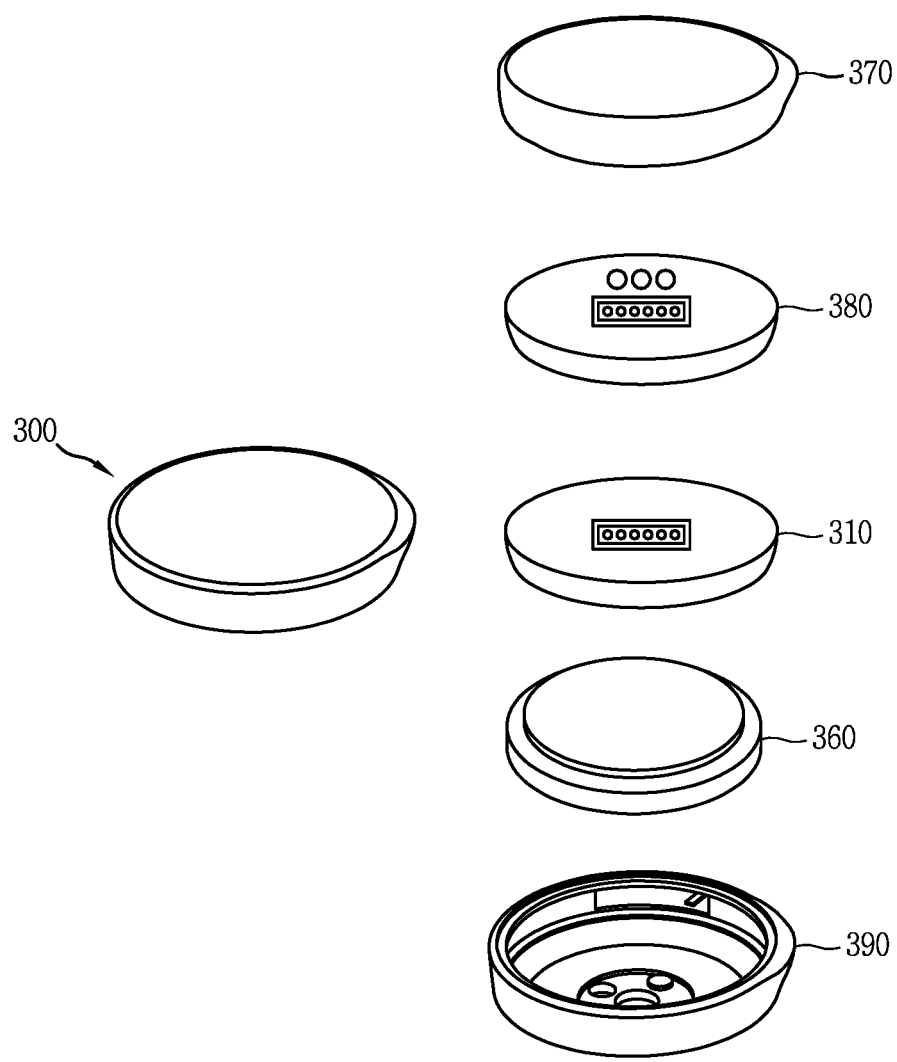

FIGS. 3A, 3B, and 3C are conceptual views illustrating a watch type mobile terminal according to an embodiment of the present disclosure. First, referring to FIG. 3A, a watch type mobile terminal according to an embodiment of the present disclosure includes a FOB module capable of controlling a vehicle.

The FOB module has a function of controlling a vehicle (or a function related to a vehicle). For example, when a user input is received through a display unit or a user input unit provided in a watch type mobile terminal, a vehicle can be controlled to perform a function related to the vehicle corresponding to the input.

The watch type mobile terminal including the FOB module can be coupled to the band 202 described above with reference to FIG. 2 so as to be used. Further, the watch type mobile terminal related to the present disclosure can serve as an electronic key for a vehicle or a smart vehicle key.

The FOB module can perform various functions provided in a smart key for an existing vehicle. For example, the FOB module can perform a vehicle door opening and closing function, a trunk opening and closing function, an emergency lamp lighting function, a Klaxon (horn) output function, an immobilizer function, and the like.

In addition, the FOB module can differentially set a control authority of the vehicle. The control authority of the vehicle can be set when the FOB module is attached to a main system, or when the FOB module is separated from the main system, the control authority of the vehicle can be set through user authentication or through a previously authenticated external terminal (for example, a mobile terminal owned by the user of the watch type mobile terminal or a mobile terminal which has performed with the watch type mobile terminal). The watch type mobile terminal according to an embodiment of the present disclosure can be termed a "FOB key", an "immobilizer key", an "electronic key", a "smart key", a "card key", or the like.

FIG. 3A is a block diagram illustrating a configuration of a watch type mobile terminal according to an embodiment of the present disclosure. Referring to FIG. 3A, the watch type mobile terminal 200 according to an embodiment of the present disclosure includes a main system 310 (or a main module or a main system module) formed as a module or a board and electrically or physically detachably attached to the FOB module described above (see FIG. 3B).

The main system 310 includes a signal processing unit 311, an interface unit 320, a communication unit 330, a memory 340, a smart key controller 350, and a power supply unit 360. The signal processing unit 311 (or the controller 180) processes a signal transferred between components of the main system 310. In addition, the main system 310 may include at least one of the components described above with reference to FIG. 1A, and the signal processing unit 311 may be, for example, the controller 180 described above with reference to FIG. 1A.

The interface unit 320 can be connected to a vehicle controller provided in the vehicle such that it performs wired/wireless communication with the vehicle controller. The interface unit 320 includes at least one button associated with a function related to the vehicle, and can receive a user command through each button. Further, the interface unit 320 can deliver a user command received through a button to the smart key controller 350 through the signal processing unit 311.

Also, the interface unit 320 can be connected to the vehicle controller (or a vehicle driving unit) wiredly or wirelessly, and can be connected to the FOB module 380 such that it performs wired/wireless communication with the FOB module 380. When a signal is received from the FOB module 380 through the communication unit 330, the interface unit 320 transmits the received signal to the vehicle controller. For example, when an ignition start signal is received from the FOB module 280, the interface unit 320 delivers the ignition start signal to the vehicle controller such that the engine of the vehicle is started. Also, the interface unit 320 may be the interface unit 160 described above with reference to FIG. 1A.

The communication unit 330 includes a communication module supporting a communication interface unit for signal transmission and reception with the FOB module 380. For example, the communication unit 330 can have a low frequency (LF) communication unit 331 transmitting an LF signal having a preset frequency band, for example, 125 kHz, 134 kHz, or the like, to the FOB module 380, and a radio frequency (RF) communication unit 332 receiving an RF signal having a preset frequency band, for example, 433 MHz, or the like, from the FOB module 380.

In addition, the communication unit 330 can further include a communication module supporting a communication interface unit for signal transmission and reception with a neighbor mobile terminal 100. For example, the communication unit 330 can have a short-range communication unit 333 transmitting and receiving a signal to and from a mobile terminal through a communication scheme such as near field communication (NFC), Bluetooth, and the like.

Also, the communication unit 330 may be the wireless communication unit 110 described above with reference to FIG. 1A. A communication unit 110 can also be provided in the FOB module 380 and/or the display unit 370, as well as in the main system 310 of the present disclosure.

The memory 340 can store a set value for an operation of the main system 310 such as frequency information of a signal of the FOB module 380 defined for signal transmission and reception with the FOB module 380. The memory 340 may include information related to a control authority to control a vehicle and information related to user authentication.

Also, the memory 340 can store a control algorithm generating a control command for controlling driving of a vehicle using a signal received from the FOB module 380. The memory 340 can also store information set for signal transmission and reception with the mobile terminal 100, and store a control algorithm for controlling power level of the mobile terminal 100. The memory 340 may be the memory 170 described above with reference to FIG. 1A.

When a function provided in the vehicle is executed, the smart key controller 350 receives a signal related to the executed function through the interface unit 220, generates a driving signal (wake-up) driving the FOB module 380, and transmits the driving signal to the FOB module 280 through the LF communication unit 331.

Further, when data of a response signal received from the FOB module 380 matches previously registered data, the smart key controller 350 determines that authentication of the corresponding FOB module 380 has been successfully performed. Thereafter, the smart key controller 350 transmits the control command, which has been input through the interface unit 320, to the FOB module 380 through the LF communication unit 331.

Further, when a start signal corresponding to a request signal is received through the RF communication unit 232, the smart key controller 350 can output a command for driving a corresponding driving unit of the vehicle through the interface unit 220 based on the start signal. In addition, when the data of the response signal received through the RF communication unit 332 does not match the previously registered data, the smart key controller 350 determines that authentication of the corresponding FOB module 380 has failed.

So far, it is described that the smart key controller 350 is a separate component, but the present disclosure is not limited thereto. Every component/function/features performed by the smart key controller 350 can be performed by the signal processing unit 311 (or the controller 180).

Also, the power supply unit 360 supplying power to the watch type mobile terminal 200 is provided. The power supply unit 360 may be a battery 360 which is installed in the watch type mobile terminal 200 or detachably formed in the watch type mobile terminal 200. The power supply unit 360 may be the power supply unit 190 described above with reference to FIG. 1A.

The battery can receive power through a power cable connected to the interface unit 320 or be wirelessly charged through a wireless charging device. Wireless charging can be implemented through electromagnetic inductive coupling or magnetic resonance.

Also, the FOB module 380 according to an embodiment of the present disclosure includes a processor or controller 382, an input unit 381, a communication unit 383, a reading unit 386, and a storage unit 387. The processor 382 (or controller) controls an operation of each component of the FOB module 380. At least one operation button can be provided in the FOB module 380, and a command corresponding to a button operated in the FOB module 380 can be input through the input unit 381.

The communication unit 383 includes a communication module supporting a communication interface for signal transmission and reception with the main system 310. For example, the communication unit 383 can have an LF communication unit 384 receiving an LF signal having a preset frequency band, for example, 125 kHz, 134 kHz, and the like, from the main system 310, and can have an RF communication unit 385 transmitting an RF signal having a preset frequency band, for example, 433 MHz, or the like, to the smart key main system 310. Further, the communication unit 383 can be the wireless communication unit 110 described above with reference to FIG. 1A.

The reading unit 386 reads a signal received through the LF communication unit 284. For example, the reading unit 386 can read a driving signal received through the LF communication unit 384, and when authentication of the FOB module 380 is completed, the reading unit 386 can read a request signal received through the LF communication unit 384. Further, the processor 382 can generate a corresponding response signal according to a reading result from the reading unit 386, and transmit the generated response signal to the main system 310 through the RF communication unit 385. Further, the processor 382 can compare the reading result from the reading unit 3386 with data stored in the storage unit 387 and generate a response signal according to the comparison result.

In other words, when the driving signal is received from the main system 310, the processor 382 can compare the reading result from the reading unit 386 with data stored in the storage unit 387. When the reading result and the data match, the processor 382 generates a response signal for acknowledging the driving signal and transmits the response signal to the main system 310. In addition, when the reading result from the reading unit 386 and the data stored in the storage unit 387 does not match, the processor 382 determines that an error has occurred, and transmits an error signal to the main system 310.

Further, a communication set value for signal transmission and reception between the FOB module 380 and the main system 310 can be stored in the storage unit 387, and information for signal generation can be stored in the storage unit 387. In addition, the display unit 370 (or a display module) displays (outputs) information processed in at least one of the FOB module 380 and the main system 310. For example, the display unit 370 can display execution screen information of an application program driven in at least one of the FOB module 380 and the main system 310 or user interface (UI) or graphic user interface (GUI) information in accordance with such execution screen information.

Also, the display unit 370 can be configured as a stereoscopic display unit displaying a stereoscopic image. Three-dimensional (3D) display method such as a stereoscopic method (glass type), an auto-stereoscopic method (glassless type), a projection method (holographic type), and the like, can be applied to the stereoscopic display unit FIG. 3B is a perspective view and an exploded perspective view of a watch type mobile terminal according to an embodiment of the present disclosure. A main body 300 or 201 of the watch type mobile terminal according to an embodiment of the present disclosure can include a FOB module 380 formed to control a vehicle.

As illustrated in FIG. 3B, the main body 300 of the watch type mobile terminal includes a display unit 370, the FOB module 380, the main system 310, the power supply unit 360, and the main frame 390. The main frame 390 can be at least one of the first case 201a and the second case 201b described above with reference to FIG. 2, or a combination thereof.

The main frame 390 serves as a case allowing at least one of the display unit 370, the FOB module 380, the main system 310, and the power supply unit (battery) 360 to be coupled. Also, the band 202 described above with reference to FIG. 2 can be coupled to the main frame 390.

FIG. 3B illustrates the main body 300 of the watch type mobile terminal 200 has a circular shape, but, without being limited thereto, the main body 300 can also have an oval shape or a polygonal shape. The main body 300 of the watch type mobile terminal according to an embodiment of the present disclosure having the aforementioned configuration can be integrally formed (first type), or at least one of the display unit 370, the FOB module 380, and the main system 310 among the components of the watch type mobile terminal can be separately formed to be independently used (operated).

For example, only the display unit can be separately used (second type) from the other remaining components, the display unit and the FOB module can be integrally formed and separately used (third type) from the other remaining components, or the FOB module can be selectively coupled to the display unit or the main system and used (fourth type).

That is, in an embodiment of the present disclosure, the display unit can be used alone, the display unit and the FOB module can be formed as a single module (or coupled) and separately used from the main system 310, or the display unit, the FOB module, and the main system 310 can be individually separated to be used. Although at least one of the display unit 370, the FOB module 380, and the main system 310 is separately used, the components have a communication unit (for example, the wireless communication unit 110 of FIG. 1A) to perform communication with each other.

In addition, the watch type mobile terminal 200 according to an embodiment of the present disclosure can interwork with another mobile terminal, e.g., a smartphone, so as to be used. For example, a mobile communication terminal and a vehicle can perform wireless communication in an LF and RF communication manner using a mobile communication network, and the watch type mobile terminal 200 and the other mobile terminal can perform wireless communication in a Bluetooth communication manner. Further, the other mobile terminal can be a smartphone in which a dedicated application associated with various functional operation units of a vehicle in an internal system thereof, and the dedicated application is driven.

Further, the smartphone, as the mobile terminal described above with reference to FIGS. 1A to 1C, can be any wireless communication device as long as it can perform wireless communication such as a mobile communication network or Bluetooth communication such as a mobile phone, a notebook computer, a digital broadcasting terminal, a personal digital assistant (PDA), a portable multimedia player (PMP), and any other table PCs. Hereinafter, for the purposes of description, the other mobile terminal will be referred to as a "smartphone", an "external device", an "external terminal", or a "preset external terminal".

Further, the FOB module 380 can be any module as long as it can perform wireless communication with a smart key control unit provided in a vehicle and apply a predetermined electrical signal, regardless of type such as a FOB key or a card type key as described above.

Hereinafter, first to fourth type use examples related to a watch type mobile terminal of the present disclosure will be described. The first to fourth types are classified according to selective coupling of the detachable FOB module 380. That is, the FOB module 380 can be coupled to the display unit 370 and the main system 310 so as to be used. Thus, a connector is provided above or below the FOB module 380, and a connection terminal electrically connected to the FOB module is provided above the main system 310.

The first type can be, for example, when the FOB module is installed in a band and used. When used as the first type, the watch type mobile terminal operates like a general smart watch and has the same appearance as that of the smart watch.

The second type can be, for example, when only the display unit 370 is separated and the FOB module 380 and the main system 310 can be coupled and connected together with a band such that the display unit 380 is installed in a preset external terminal. For the second type, the display unit 370 can be disposed on (coupled or attached to) a rear surface of the preset external terminal to provide a display unit, different from a front display unit provided on a front side of the terminal body, to a rear side of the terminal body. Hereinafter, the display unit provided on the preset external terminal will be referred to as a first display unit and the display unit 380 provided on the watch type mobile terminal 200 will be referred to as a second display unit.

The second display unit provided on the rear side of the mobile communication terminal has a small size, and thus can simply display information regarding a user or a vehicle. Further, the second display unit can input information based on a touch, like the first display unit.

Further, for the second type, the FOB module 380 coupled to the band can be used without a display, and simple information can be output by an output unit other than the second display unit. Also, since the FOB module 380 is coupled to the band, the watch type mobile terminal 200 can serve as an activity tracker. For example, the watch type mobile terminal 200 without the display unit can be simply used as a pedometer or can perform a healthcare function by a heart rate sensor, or the like. However, since the FOB module 380 is coupled to the band, it is possible to control an external device (vehicle).

In addition, the third type is when the second display unit 370 is coupled to the FOB module 380 and the FOB module 380 and the main system 310 are separately used. For example, the FOB module 380 and the display unit 370 separated from the main system 310 can be installed on a rear surface of a preset external terminal so as to be used. Further, since the FOB module 380 is also coupled (connected or attached) to the preset eternal terminal, in addition to the second display unit 370, an external device (vehicle) can be controlled through the preset external terminal. Also, a series of information and a user information controlling the external device (vehicle) can also be displayed on the second display unit 370.

Further, even though the main system is connected to the band and the FOB module 380 is separated, the external device (vehicle) can be controlled. For example, a function of controlling the external device (vehicle) provided in the FOB module 380 can also be provided in the main system 310. Thus, even though the FOB module 380 is separated from the main system 310, the user can perform controlling on the external device (vehicle) using the main system 310.

Further, in the present disclosure, different control authorities can be set in the FOB module 380 and the main system 310. For example, a first control authority for performing only a predetermined function provided in an external device can be set in the FOB module 380, and a second control authority, higher than the first control authority, for performing every function provided in an external device can be set in the main system 310.

In addition, when a control authority function regarding an external device is set only in the FOB module 380, the main system 310 coupled to the band can perform only a predetermined function such as an activity tracker.

Also, the fourth type can be a type in which the display unit 370, the FOB module 380, and the main system 310 are all separable, and can be a type which can be individually used. Thus, the FOB module 380 can be coupled to the main system 310 so as to be used, and can be coupled to the display unit 370 so as to be used, or can be used autonomously.

The fourth type can be when an installation position of the FOB module 380 is selectively switchable. When the FOB module 380 is coupled to the main system and used, it can be similar to the second type described above, and when the FOB module is coupled to the second display unit and used, it can be similar to the case of the third type described above.

A battery and a predetermined processor can be provided in each of the display unit 370 and the FOB module 380 such that at least one of the display unit 370 and the FOB module 380 can be separated and used according to the second to fourth types. Also, the display unit 370, the FOB module 380, and the main system 310 can each have a wireless communication unit 110 to communicate with each other.

Figure 4:
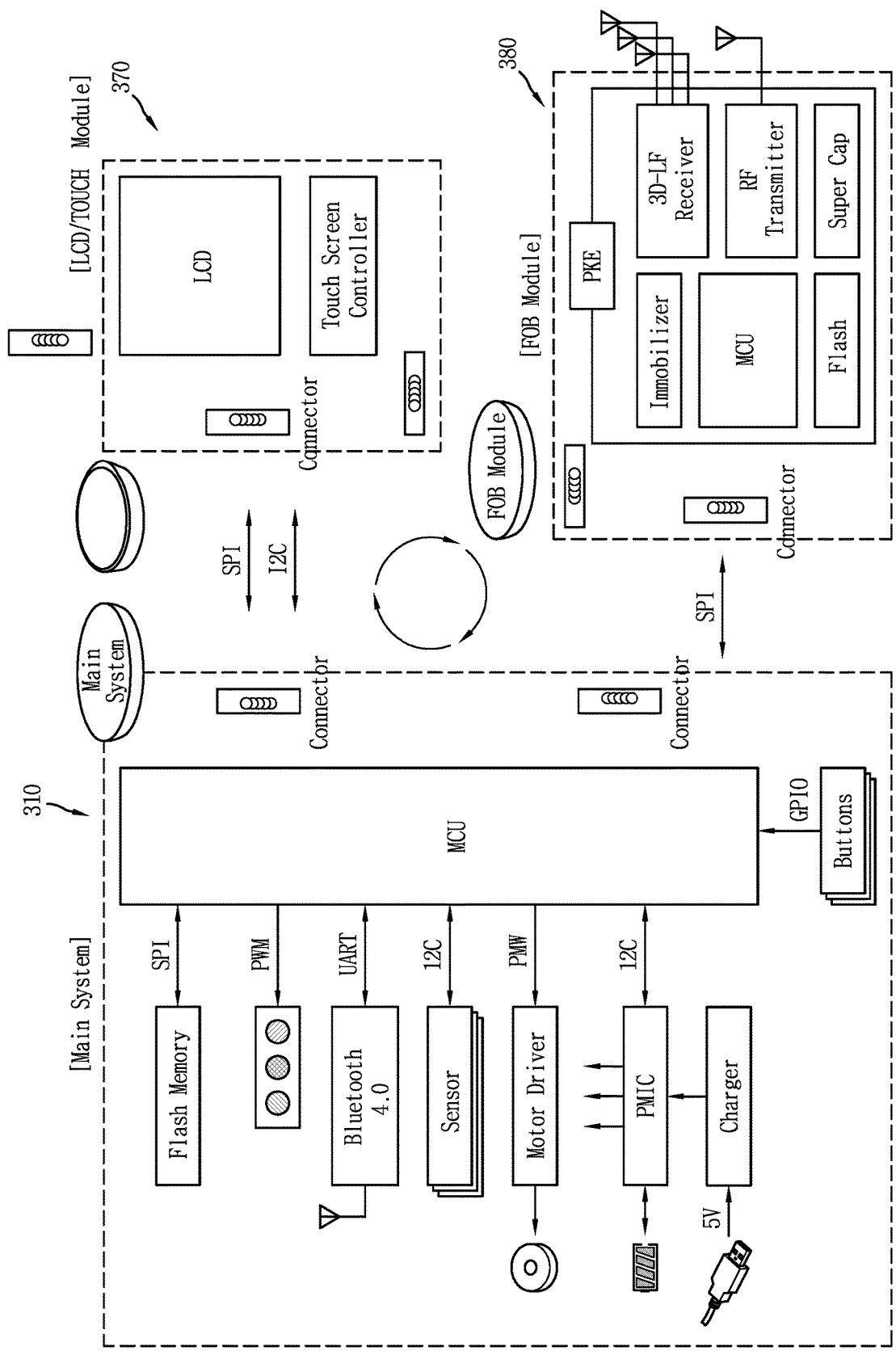
FIG. 4 is a circuit diagram of a watch type mobile terminal according to an embodiment of the present disclosure.

Next, FIG. 4 is a circuit diagram of a watch type mobile terminal according to an embodiment of the present disclosure. As described above, the watch type mobile terminal 200 related to the present disclosure can include a band 202 worn on a user's wrist to surround the wrist, a main frame 390 connected to the band 202, a main system 310 provided in the main frame 390, a FOB module 380 formed to be detachably attached to the main system, and a display unit 370 formed to be detachable from the FOB module 380.

As illustrated in FIG. 4, the main system 310 can include a flash memory, an LED module, a short-range communication module (Bluetooth0, a sensor, a motor driver, a power management integrated circuit (PMIC), a charging module (charger), an input unit (buttons), and an MCU (controller). These components can be at least one of the components described above with reference to FIGS. 1A to 1C.

Also, the display unit 370 (or a display module) can include an LCD module, a touch screen controller, and the like. Also, the FOB module 380 can include an immobilizer, an MCU, an LF reception unit, an RF transmission unit, a capacitor, a flash memory, and the like. The main system 310 and the display unit 370 can each have a connector to be electrically connected to the FOB module 380.

A first connector to electrically connected with the main system 310 can be provided on one surface of the FOB module 380, and a second connector to be electrically connected to the display unit 370 can be provided on the other surface opposing the one surface of the FOB module 380. In this disclosure, "coupling (connecting or attaching) a component A and a component B" can refer to electrical coupling the component A and the component B, as well as physical coupling the component A and component B.

Also, in this disclosure, "separating the component A and the component B" can refer to "electrically separating the component A and the component B, as well as physically separating the component A and the component B. Further, the component A and the component B can be at least one of the main system 310, the display unit 370, and the FOB module 380 include din the watch type mobile terminal of the present disclosure.

When the components are electrically connected to each other through the connector described above, data can be transmitted and received therebetween through a serial communication technique such as a serial peripheral interface (SPI) communication technique and an inter-integrated circuit (I2C) communication technique in an embodiment of the present disclosure.

The main system 310, the FOB module 380, and the display unit 370 can have a wireless communication unit. The wireless communication unit can be the wireless communication unit described above with reference to FIG. 1A, for example. When at least one of the main system 310, the FOB module 380, and the display unit 370 is coupled, the coupled components can perform communication through a connector.

In addition, when at least one of the FOB module 380 and the display unit 370 is separated, the separated modules can perform wireless communication through the wireless communication unit. Each of the FOB module 380 and the display unit 370 can be formed to be detachably attached to an external device.

For example, an external device can have a connector, and the connector of the external device can be connected to a first connector (or second connector) of the FOB module 380 or can be connected to a connector of the display unit 380. Also, the external device and the FOB module 380 or the external device and the display unit 370 can be physically attached.

The external device can include any type electronic device which can communicate with the watch type mobile terminal of the present disclosure. For example, the external device can be the external device (FIGS. 1A to 1C) or a vehicle. In addition, a control authority for controlling the external device can be set in at least one of the main system 310, the FOB module 380, and the display unit 370.

When the control authority is set, the external device can be controlled based on attachment of a module separated from the watch type mobile terminal 200 or through wireless communication with the separated module. In addition, in the watch type mobile terminal 200 related to the present disclosure, the main system 310 and the FOB module 380 can be coupled and the FOB module 380 can be coupled to the display unit 370, but the present disclosure is not limited thereto.

As illustrated in FIG. 4, the display unit 370 can be detachably attached to the main system 310. Further, only the FOB module 380 can be separated and the display unit 370 and the main system 310 can be coupled. In this instance, the display unit 370 and the main system 310 can be electrically connected through a connector of the display unit 370 and a connector of the main system 310, and the FOB module 380 separated from the main system 310 (or the display unit 370) can perform wireless communication through a wireless communication unit.

A type performed through this coupling can be defined as a "fifth type." That is, as illustrated in FIG. 3C, the watch type mobile terminal related to the present disclosure can operate in at least one of the first type in which all the main system 310, the FOB module 380, and the display unit 370 are coupled, the second type I which the main system 310 and the FOB module 380 are coupled and the display unit 370 is separated from the FOB module, the third type in which the FOB module 380 and the display unit 370 are coupled and the FOB module 380 is separated from the main system 310, and the fourth type in which all of the main system 310, the FOB module 380, and the display unit 370 are separated. Also, the watch type mobile terminal related to the present disclosure can also be operated in the fifth type in which only the FOB module 380 is separated and the main system 310 and the display unit 370 are coupled.

Figure 5:
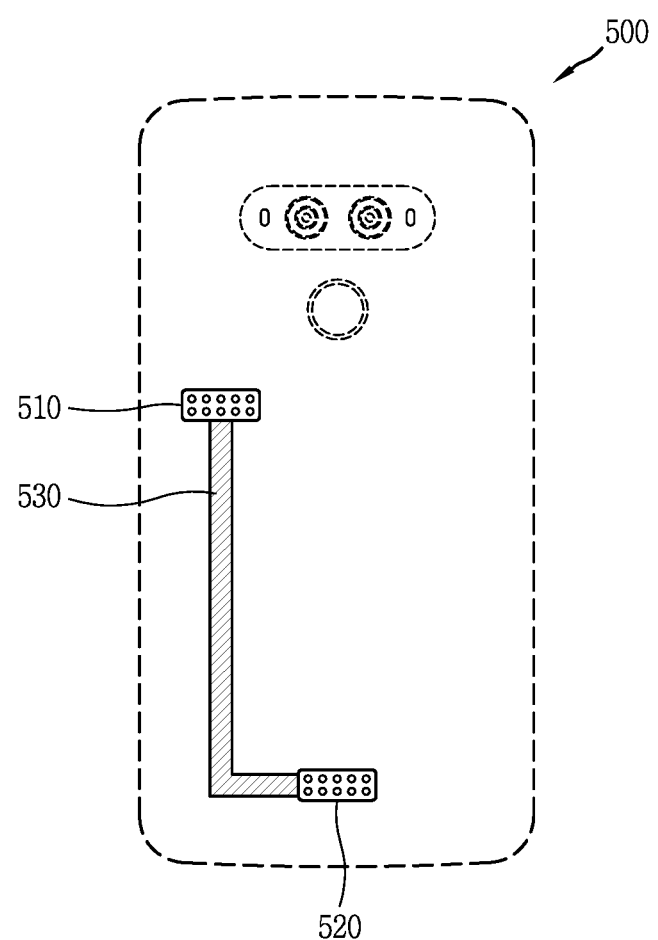
FIG. 5 is a conceptual view illustrating an external device to which a module separated from a watch type mobile terminal according to an embodiment of the present disclosure is attached.

Next, FIG. 5 is a conceptual view illustrating an external device to which a module separated from a watch type mobile terminal according to an embodiment of the present disclosure is attached. In FIG. 5, an external device 500 as an embodiment of an external device is illustrated. The external terminal 500 can be the mobile terminal described above with reference to FIGS. 1A to 1C.

The external terminal 500 (mobile terminal 100) can have at least one connector 510 and 520 (or Appsport) to which an external module is attachable. When the connector is in plurality, the plurality of connectors can be implemented to be connected by a circuit board (e.g., a flexible printed circuit board (FPCB)) such that they communicate with each other.

The FOB module 380 or the display unit 370 separated from the watch type mobile terminal 200 related to the present disclosure can be connected to the external terminal 500. Further, the FOB module 380 can have different control authorities according to a type (or position) of a coupled connector among a plurality of connectors provided in the external terminal.

For example, when the FOB module 380 is coupled to the first connector 510 of the external terminal, a first control authority for controlling an external device can be set in the FOB module 380, and when the FOB module 380 is coupled to a second connector 520 different from the first connector 510 of the external terminal, a second control authority different from the first control authority can be set.

Also, the display unit 370 can display different types of screen information according to a type (or position) of coupled connector among a plurality of connectors provided in the external terminal. For example, when the display unit 370 is coupled or connected to the first connector of the external terminal, the display unit 370 can display first screen information, and when the display unit 370 is coupled or connected to a second connector different from the first connector of the external terminal, the display unit 370 can output second screen information different from the first screen information.

Also, the watch type mobile terminal related to the present disclosure can perform different functions according to whether the FOB module 380 or the display unit 370 is individually attached to an external device (external terminal 500) or whether the FOB module 380 and the display unit 370 in a coupled state is attached to the external device (external terminal 500).

For example, when the FOB module 380 is attached to the external terminal 500, the FOB module 380 can perform a first function, and when the display unit 370 is attached to the external terminal, the display unit 370 can perform a second function different from the first function. Also, when the FOB module 380 and the display unit 370 in a coupled state are attached to the external terminal 500, a third function different from the first and second functions can be performed.

For example, the first to third functions can include a control authority, screen information, a control method, and the like, and the first to third functions may not be always different but at least one thereof may be the same/similar function. In addition, in the watch type mobile terminal 200 related to the present disclosure, the FOB module 380 can be selectively coupled to any one of the main system 310 and the display unit 370. In this instance, a control authority of an external device (e.g., a vehicle) granted to (or set in) the FOB module 380 can be varied.

For example, when the FOB module 380 is coupled to the main system 310 and separated from the display unit 370 (in the case of the second type), a first control authority can be granted. Also, when the FOB module 380 is separated from the main system 310 and coupled to the display unit 370 (in the case of the third type), a second control authority different from the first control authority can be granted.

For example, the first control authority set in (or granted to) the FOB module 380 can be a control authority to control every function of a vehicle. In another example, the second control authority set in (or granted to) the FOB module 380 can be a control authority to limit a predetermined function or a predetermined operation of a vehicle. For example, when the second control authority is set in a second main body, opening of a specific box of a vehicle can be limited, some of functions of vehicle navigation can be limited, or a driving speed, a driving range, and the like, of the vehicle can be limited.

The control authority can also be set in (or granted to) the main system 310 or the display unit 370, as well as being set in (or granted to) the FOB module 380. Also, the main system 310 can change a control authority set in the separated FOB module 380 or the display unit 370 or nullify the same. Such a change or nullification of the control authority can be performed through a wireless communication unit.

Hereinafter, as illustrated in (b) of FIG. 3C, when the watch type mobile terminal 200 related to the present disclosure is used as the second type in which only the display unit 370 is separated will be described as an example. When the display unit 370 is separated from the watch type mobile terminal 200 related to the present disclosure, that is, when the display unit 370 is separated from the FOB module 380 and attached to an external device, screen information related to the external device to which the display unit 370 is attached can be displayed on the display unit 370.

For example, when the display unit 370 is attached to a vehicle, screen information related to the vehicle can be displayed on the display unit 370. In another example, when the display unit 370 is attached to an external terminal (mobile terminal), screen information related to the external terminal can be displayed on the display unit 370.

Such screen information can be displayed on the display unit 370 under the control of a controller of the external device or can be displayed on the display unit 370 under the control of a processor included in the display unit 370. In addition, although the display unit 370 is attached to the external device, screen information related to the watch type mobile terminal 200 can be displayed on the display unit 370. Further, the screen information related to the watch type mobile terminal 200 can be screen information related to a function that can be performed in the main system 310 or the FOB module 380.

In order to be displayed on the display unit 370, the screen information related to the watch type mobile terminal 200 can be transmitted to the display unit 370 (or the external device) from the main system 310 or the FOB module 380 through a wireless communication unit, or can be previously stored in a memory of the display unit 370.

In addition, the watch type mobile terminal 200 related to the present disclosure can display information related to information sensed through the sensing unit 140 provided in the watch type mobile terminal 200, on at least one of a touch screen of the external device and the display unit 370 attached to the external device.

Figure 6:
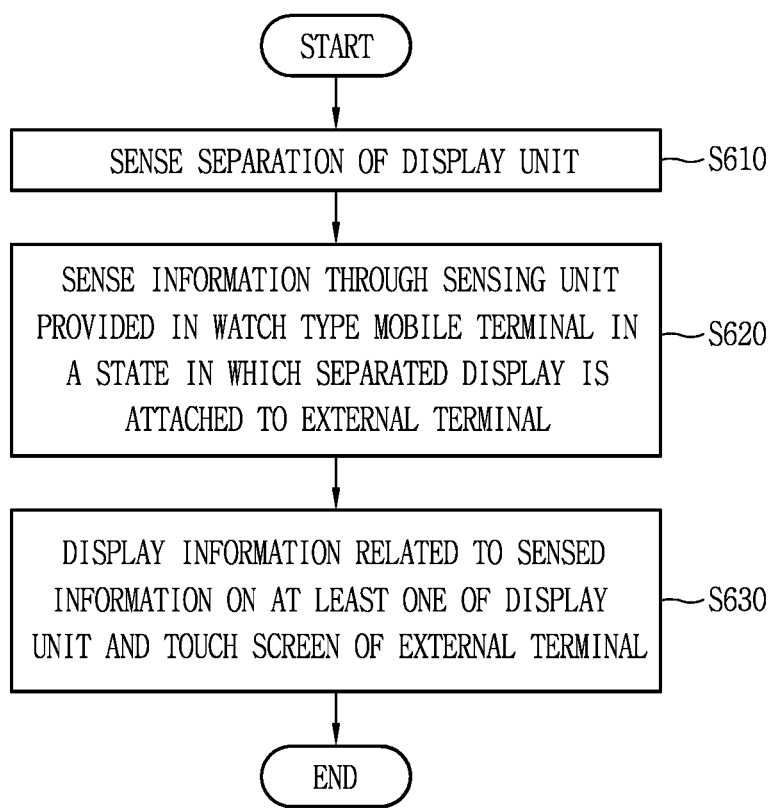
FIG. 6 is a flow chart illustrating a control method according to an embodiment of the present disclosure.
Figure 7A:
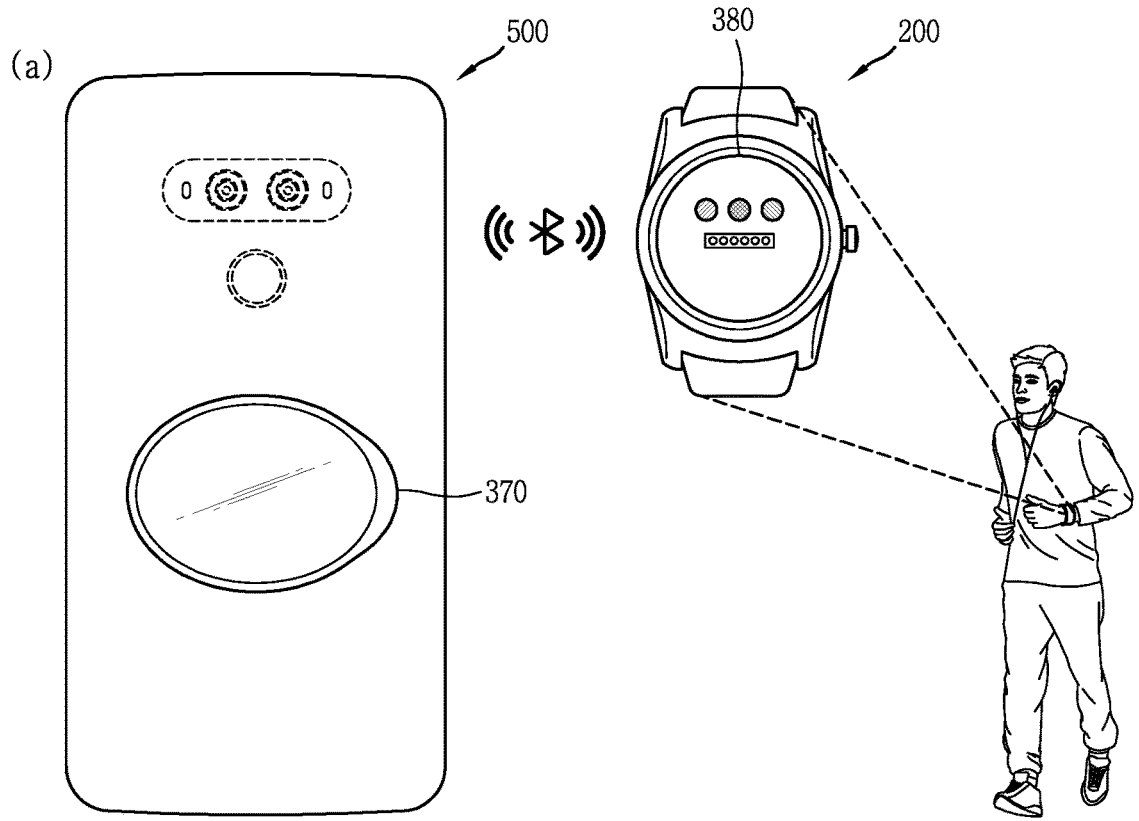
FIGS. 7A and 7B are conceptual views illustrating the control method of FIG. 6.
Figure 7A:
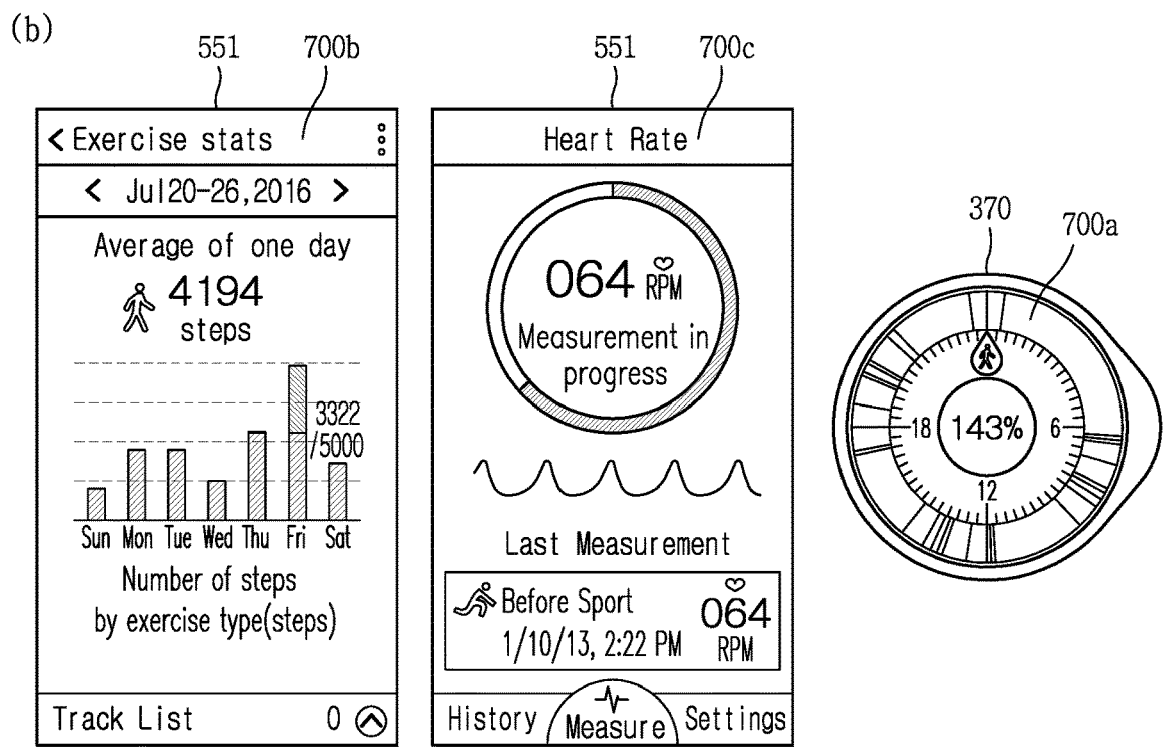
Figure 7B:
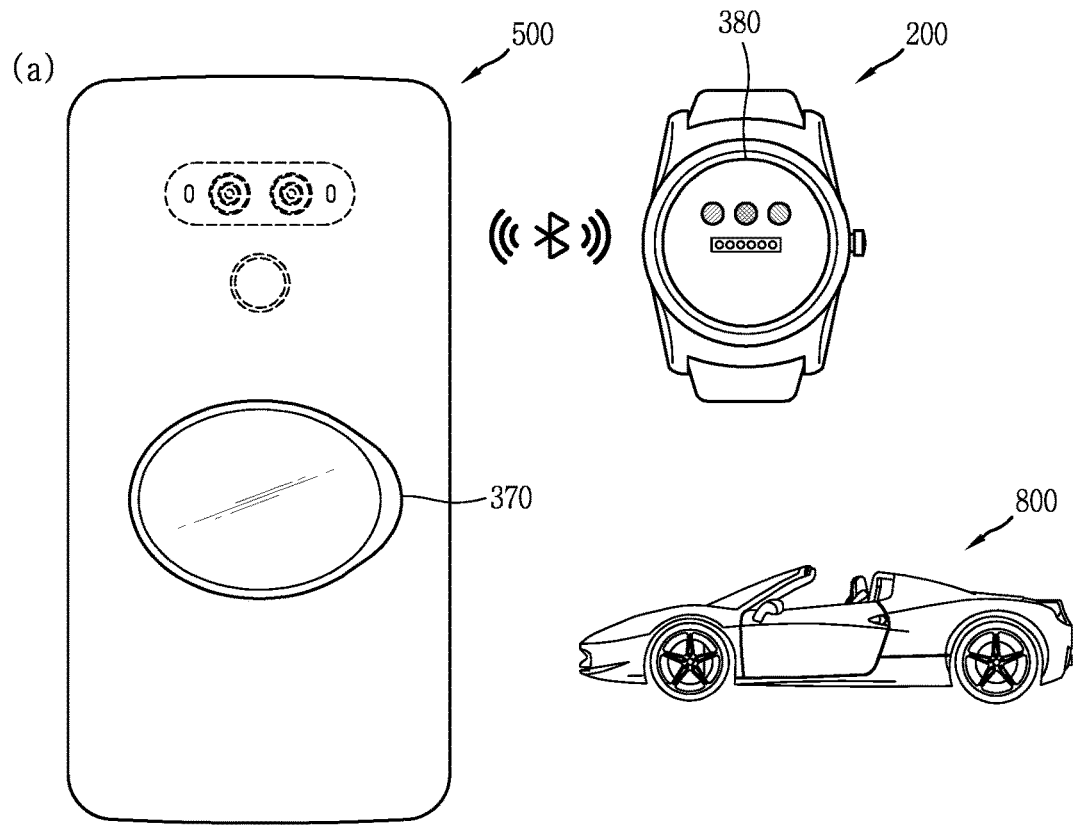
Figure 7B:
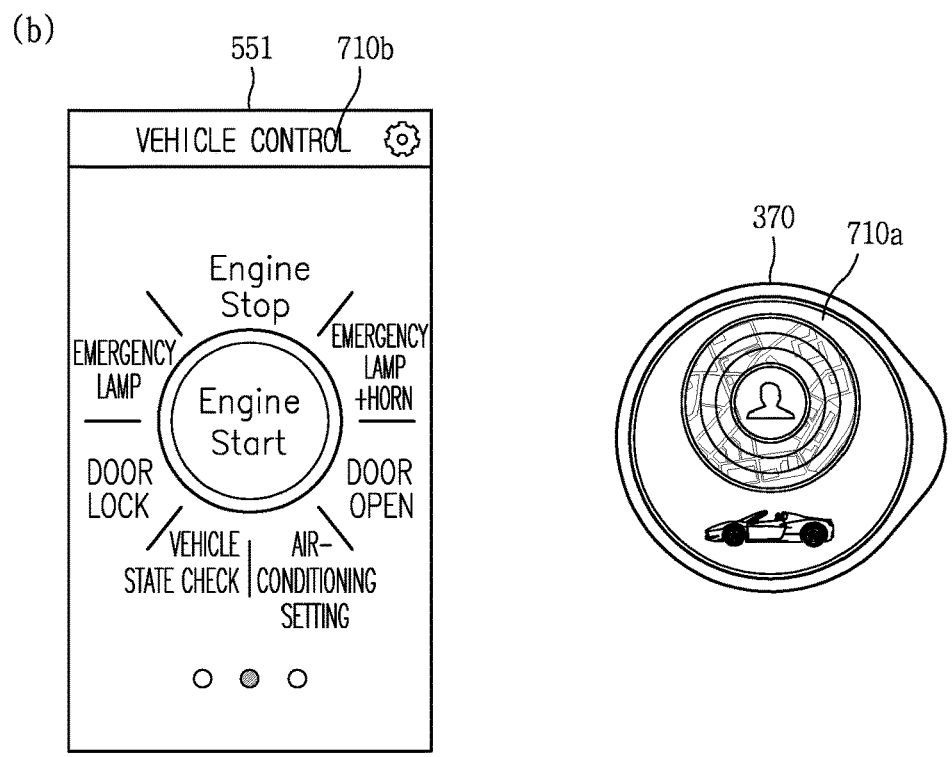

Next, FIG. 6 is a flow chart illustrating a control method according to an embodiment of the present disclosure, and FIGS. 7A and 7B are conceptual views illustrating the control method of FIG. 6. First, in the present disclosure, the display unit 370 being separated from the FOB module 380 is sensed (S610).

For example, a controller of the main system 310 or a processor of the FOB module 380 can sense that the display unit 370 is separated from the FOB module 380 by a user.

In another example, at least one of the FOB module 380 and the main system 310 can include the sensing unit 140 described above with reference to FIG. 1A, and the controller of the main system 310 or the processor of the FOB module 380 can sense that the display unit 370 is separated, through the sensing unit 140.

Thereafter, when the separated display unit 370 is attached to the external terminal, information can be sensed through the sensing unit 140 provided in the watch type mobile terminal (i.e., the sensing unit 140 provided in at least one of the FOB module 380 and the main system 310 (S620).

Further, a type of the sensed information can vary according to a type of a sensor provided in the sensing unit 140. Also, when the display unit 370 is separated from the FOB module 380 and attached to the external terminal 500, the processor of the display unit 370 can transmit information indicating that the display unit 370 has been attached to the external terminal 500, to the processor of the FOB module 380 or the controller of the main system 310 through a wireless communication unit.

Also, the processor of the display unit 370 can transmit information related to a type of the external terminal 500 to which the display unit 370 is attached, identification information, and a type (or a position) of a connector attached in the external terminal 500, to the FOB module 380 or the main system 310 through the wireless communication unit.

Thereafter, in the present disclosure, information related to the information sensed by the sensing unit 140 can be displayed in at least one of the display unit 370 attached to the external terminal 500 and a touch screen of the external terminal 500 (S630). For example, when information indicating that the display unit 370 has been attached to the external terminal (or the external device) is received through the wireless communication unit, the controller of the main system 310 or the processor of the FOB module 380 can switch the sensing unit 140 from a deactivated state to an activated state.

For example, as illustrated in (a) of FIG. 7A, when the display unit 370 is separated from the watch type mobile terminal 200 and attached to the external terminal 500, the processor of the FOB 380 (or the controller of the main system 310) can sense information through the sensing unit 140. The processor of the FOB module 380 (or the controller of the main system 310) can determine (or extract or sense) a state of the user who wears the watch type mobile terminal 200 based on the sensed information.

Thereafter, the processor of the FOB module 380 (or the controller of the main system 310) can transmit the determined state information of the user to at least one of the external terminal 500 and the display unit 370 through the wireless communication unit. The controller of the external terminal 500 can determine an application program (application) to be executed and execute the determined application program, based on the received state information of the user.

Also, the processor of the FOB module 380 (or the controller of the main system 310) can transmit the sensed information (data) to at least one of the external terminal 500 and the display unit 370 through the wireless communication unit. Thereafter, information 700a, 700b, and 700c related to the sensed information can be displayed on at least one of the display unit 370 and the touch screen 551 of the external terminal 500.

Further, as illustrated in (b) of FIG. 7A, the information related to the sensed information can be screen information reflecting the sensed information in an execution screen of the executed application program (application). The information 700a displayed on the display unit 370 and the screen information 700b and 700c output on a touch screen 551 of the external terminal 500 can be different. This is because a position and a size in which the display unit 370 is attached and a position and a size of the touch screen 551 of the external terminal 500 can be different.

Through this configuration, in the watch type mobile terminal of the present disclosure, when the display unit 370 is separated and attached to an external terminal, information (screen information) related to information sensed through the sensing unit provided in the watch type mobile terminal can be displayed in at least one of the display unit 370 and the touch screen 551 of the external terminal, providing a new type mobile terminal.

In addition, a control authority to control an external device (vehicle) can be set in the display unit 370. When the display unit 370 in which a control authority is set is separated from the FOB module 380 of the watch type mobile terminal 200 and attached to the external terminal 500 as illustrated in (a) of FIG. 7B, screen information 710a and 710b for controlling the external device (vehicle 800) can be displayed on the touch screen 551 of the external terminal 500 and the display unit 370 attached to the external terminal 500.

Further, the screen information 710a and 710b can be varied according to a control authority set in the display unit 370, and the screen information 710b displayed on the touch screen 551 and the screen information 710a displayed on the display unit 370 can be different. For example, the screen information 710b displayed on the touch screen 551 can include a plurality of (various types of) vehicle 800 control function graphic objects, and the screen information 710a displayed on the display unit 730 can include some (e.g., a frequently used function) of the plurality of vehicle control function graphic objects.

In the present disclosure, a user interface enabling the user to easily control the vehicle using the screen information 710b displayed on the touch screen 551 or the screen information 710a displayed on the display unit 370. Through such a configuration, the present disclosure provides a novel watch type mobile terminal in which at least one of the main system, the FOB module, and the display unit is separable and the separated component is formed to be attachable to an external device.

Also, when the display unit is attached to the external device, the present disclosure provides the watch type mobile terminal capable of expanding a display space of the external device, by outputting at least one of information related to the external device to which the display unit is attached and information related to the watch type mobile terminal, on the display unit.

As illustrated in (c) of FIG. 3C, the watch type mobile terminal 200 related to the present disclosure is used as the third type in which the main body 300 is separated into a first main body and a second main body. The first main body can include the main frame 390, the power supply unit 360, and the main system 310. Also, the second main body can include the FOB module 380 and the display unit 370 (or a display module).

At least one of the FOB module 380 and the display unit 370 of the second main body can have a battery. Thus, although the second main body is separated from the first main body, the second main body can be driven by the battery. The controller 180 described above with reference to FIG. 1A can be provided in the first main body, for example.

For example, the controller 180 can be provided in the main system 210 to control the first main body and the second main body.

In addition, at least one of the FOB module 380 and the display unit 370 included in the second main body can have a processor. Based on a signal (or a user input) received through the FOB module 380 and the display unit 370, the processor can control the external device or can transmit predetermined information to the controller 311 or 180 provided in the first main body.

Also, each of the first main body and the second main body (the display unit 370 and the FOB module 380) can have the wireless communication unit 110 described above with reference to FIG. 1A. Thus, the first main body and the second main body can communicate with each other through at least one of the various communication methods described above or can communicate with the external device.

Also, each of the first main body and the second main body (the display unit 370 and the FOB module 380) can have the sensing unit 140 described above with reference to FIG. 1A. Thus, although the first main body, the display unit 370, and the FOB module 380 are separated in any form, the separated components can autonomously sense information that can be sensed through a sensor using the corresponding sensor included in the sensing unit 140.

When the separated second body is attached to the external device, the processor 382 can perform different functions based on types of the external device to which the second body is attached. Further, the external device can include any type of device (or object) formed to attach (or connect) the second main body.

For example, when the external device is a first device (vehicle), the processor 382 can control the second main body to perform a function related to the vehicle. For example, the processor 382 can control the second main body to perform at least one of an output function of outputting information related to the vehicle, a sensing function of selecting information related to the vehicle through the sensing unit provided in the second main body, and a control function of controlling the vehicle.

In another example, when the external device is a second device (mobile terminal (or another terminal which has not been authenticated), the processor 382 can control the second main body to perform a function related to the mobile terminal. For example, the processor 382 can control the second main body to perform an output function of outputting information related to the mobile terminal, a processing function of processing a task requested in the mobile terminal, a payment function, a user authentication function, and the like.

Also, the processor 382 can distinguish users according to a type of the mobile terminal to which the second main body is attached, and differently set a control authority such that the distinguished users can differently control the vehicle. In another example, when the second main body is separated and simply attached to a band, rather than to an electronic device, the processor 382 can control the second main body to perform a relatively simple function such as a function of obtaining biometric information of a human body contacted by the second main body, a sleep management function, a date/time/calendar output function, a pace counter function, and the like.

Also, when the external device is a device required to be controlled, the second main body can control the external device based on at least one of a user control command input through the display unit 370 or the FOB module 380 provided in the second main body and a control command received through the first main body.

In addition, the watch type mobile terminal related to the present disclosure can control a control authority of the second main body differently in consideration of whether the first main body is separated from the user's wrist, as well as whether the second main body is separated from the first main body. When the electrical connection is cut off, the controller 180 of the first main body can determine (sense, detect, or extract) that the first main body and the second main body are separated from each other.

The first main body can have the sensing unit 140 described above with reference to FIG. 1A. The controller 180 of the first main body can determine that the first main body and the second main body have been separated using various sensors included in the sensing unit 140.

The controller 810 can determine (sense, detect, or extract) whether the first main body is worn on the user's wrist or whether the first main body has been separated from the user's wrist (whether the first main body is not worn on the user's wrist) through the sensing unit 140. For example, when the sensing unit 140 is in contact with the human body (e.g., the wrist) or when a distance between the sensing unit 140 and the human body is within a predetermined distance, the controller 180 can determine that the first main body is worn on the wrist.

In another example, when the sensing unit 140 is not in contact with the human body and a distance between the sensing unit 140 and the human body is not within the predetermined distance, the controller 180 can determine that the first main body is not worn on (or separated from) the wrist. The controller 180 can set differently a control authority for the second main body to control the external device in consideration of whether the first main body is worn on the wrist and whether the first main body and the second main body are connected.

In more detail, different control authorities can be set in the second main body when the first main body is worn on the wrist and the first main body and the second main body are connected (a first case), when the first main body is separated (not worn) from the wrist when the first main body and the second main body are connected (a second case), and when the second main body is separated from the first main body when the first main body is worn on the wrist (a third case).

For example, when the first main body is worn on the wrist by the band 502 and the first main body and the second main body are connected (the first case), the controller 180 can set a control authority for controlling the external device to a first control authority (1Level) in the second main body.

Also, when the first main body and the second main body are connected but the first main body is not worn on the wrist (the second case), the controller 180 can set the control authority to a second control authority (2Level) different from the first control authority. Also, when the first main body and the second main body are separated (the third case), the controller 180 can set the control authority to a third control authority (3Level) different from the first and second control authorities.

Further, the third control authority (3Level) can be a control authority lower than the first and second control authorities, and the second control authority (2Level) can be a control authority lower than the first control authority (1Level). That is, 1Level is a highest control authority, and 2Level and 3Level can be set to be sequentially lower.

In addition, when the second main body separated from the first main body is coupled to the third main body 540, not to the first main body (a fourth case), the controller 180 can maintain a control authority to control the external device as the third control authority (3Level). Further, the third main body can refer to the first main body which can be coupled to the second body and worn on someone else (or a user who has not been authenticated).

In the above, it is described that the first control authority is maintained in the first case, the second control authority is maintained in the second case, the third control authority is maintained in the third case, and the third control authority is maintained in the fourth case, but the present disclosure is not limited thereto.

For example, in the second case, the third control authority can be set in the second main body, and in the third case, the second control authority can be set in the second body. Thus, in the present disclosure, a control authority can be variously set based on whether the first main body is worn on the wrist or whether the second main body is connected to the first main body.

Also, in the present disclosure, various applications can be performed. For example, even though the separated second main body is connected to the third main body 540, when authentication of a user who wears the third main body 540 is performed, the third control authority can be changed to a different control authority (e.g., the second control authority).

The external device described above, that is, the external device that can be controlled by the second main body can be, for example, a vehicle. For example, the first control authority set in (or granted to) the second main body can be a control authority capable of controlling every function of a vehicle.

In another example, the second control authority set in (or granted to) the second main body can be a control authority to limit a predetermined function or a predetermined operation of the vehicle. For example, when the second control authority is set in the second main body, opening of a specific box of the vehicle can be limited, some of functions of vehicle navigation can be limited, or a driving speed, a driving range, and the like, of the vehicle can be limited.

In another example, the third control authority set in (or granted to) the second main body can be a control authority to limit more functions/operations that those of the second control authority. A function/operation limited by each control authority can be determined by a user setting.

In addition, when a user of the wrist wearing the first main body by a band is an authenticated user, the controller 180 can set the first control authority in the second main body. That is, the controller 180 can set differently the control authority of the second main body controlling an external device based on whether the user of the wrist wearing the first main body by the band 502 is an authenticated user.

For example, even though the first main body is worn on the wrist by the band and the second main body and the first main body are connected (the first case), only when the user who wears the first main body is an authenticated user, the controller 180 can set (or grant) the first control authority in the second main body.

When the user who wears the first main body is a non-authenticated user in the first case, the controller 180 can set a control authority (e.g., a second or third control authority) different from the first control authority in the second main body. When a preset condition is met, the controller 180 can determine whether the user who wears the first main body by the band 502 is an authenticated user.

For example, a biometric sensor can be provided in at least one of the first main body and the second main body.

The controller 180 can determine whether the user who wears the first main body is an authenticated user using the biometric sensor. Further, for example, the authenticated user can refer to an owner of the watch type mobile terminal 200, or can be someone else previously set (registered) by the owner to use the watch type mobile terminal.

At least one of the first main body and the second main body can have a memory, and biometric information of each user can be previously stored in the memory. The controller 180 can obtain biometric information of the user who wears the first main body using the biometric sensor, and can perform user authentication using the obtained biometric information and the previously stored biometric information.

For example, when the obtained biometric information and the previously stored biometric information match, the controller 180 can determine that the user who wears the first main body is an authenticated user. In another example, when the user wears the first main body, when user authentication is successful in a preset external terminal (or a previously authenticated external terminal), the controller 180 can determine the user who wears the first main body as an authenticated user.

Further, the preset external terminal (or the previously authenticated external terminal) can be a mobile terminal owned by the owner of the watch type mobile terminal 200, a mobile terminal connected to communicate with the watch type mobile terminal 200, a mobile terminal authenticated to communicate with the watch type mobile terminal 200, and the like.

For example, the preset external terminal can be implemented in such a form as described above with reference to FIG. 1B, and can perform user authentication (e.g., fingerprint recognition, iris recognition, and the like) using a fingerprint recognition sensor, a camera, and the like. When the user authentication is successful when the user wears the first main body, the controller 180 can determine that the user who wears the first main body as an authenticated user.

Also, based on a distance between the preset external terminal and the first main body, the controller 180 can determine whether the user who wears the first main body is an authenticated user. When a distance between the first main body and the preset external terminal is within a predetermined distance, the controller 180 can determine that the user who wears the first main body is an authenticated user.

For example, the predetermined distance can be a distance within which the first main body and a preset external terminal can perform communication with each other. However, the present disclosure is not limited thereto and the predetermined distance can be a distance set by the user or can be varied.

For example, when the preset external terminal is preset within the distance over which the preset external can communicate with the first main body, the user who wears the first main body can be determined as an authenticated user. In addition, although the first main body is not worn, if a distance between the first main body and the preset external terminal is within the predetermined distance (e.g., a communication-available distance), the controller 180 can determine that the user who owns the first main body as an authenticated user.

When a user who wears the first main body is an authenticated user when the first main body and the second main body are coupled, the controller 180 can set a control authority for the second main body 510 to control the external device, to the first control authority. In addition, when the separated second main body is attached to an external device (e.g., a vehicle), the watch type mobile terminal related to the present disclosure can control the external device. However, the present disclosure is not limited thereto and when the second main body is present within the external device or when the second main body is present within a predetermined distance from the external device (within a communication-available distance), the external device can be controlled.

The processor 382 of the second main body can perform a different function according to a position in which the second main body is attached to the vehicle. For example, the second main body separated from the first main body can be installed in various modules provided in the vehicle.

When the second main body is attached to a first module of the vehicle, the processor 382 can perform a function related to the first module, and when the second main body is attached to a second module different from the first module, the processor 382 can perform a function related to the second module. Also, according to whether user authentication is successful when the second main body is attached to a start button 610, the processor 382 can differently set a control authority of the vehicle.

The user authentication can be, for example, fingerprint recognition (or fingerprint authentication). The second main body can have a fingerprint recognition sensor. The fingerprint recognition sensor can be provided in the display unit 370, for example. When the second main body is installed in one module (e.g., the first module (start button)) of the vehicle (or when the second main body is installed in one module of the vehicle and subsequently pressurized), the processor 382 can activate the fingerprint recognition sensor.

Also, when fingerprint authentication is successful, the processor 382 can set a first control authority to control every function of the vehicle. In addition, when fingerprint authentication fails, the processor 382 can set a second control authority to limit opening of a specific box of a vehicle, to limit some of functions of vehicle navigation, or to limit a driving speed, a driving range, and the like, of the vehicle.

When the second main body is attached to the start button, the second main body can be used as a start key. Also, when the second main body is attached to the start button, the second main body can transmit whether the start button is attached, to the first main body. Thus, when the second main body is handed over to someone else, the first main body can monitor a usage state of the second main body in real time.

Also, after the second main body is attached to the start button, when the vehicle starts driving, the second main body can transmit information related to driving of the vehicle to the first main body. When the second main body is attached to one module (e.g., an OD charger, a lighter socket) of the vehicle, the processor 382 of the second main body can output one (e.g., vehicle inside information) of pieces of information related to the vehicle on the display unit 370.

Further, when new information is sensed through an OBD module (e.g., vehicle outside information), the processor 382 can control the display unit 370 to display the sensed vehicle outside information. The vehicle inside information can include acceleration information, coolant information, engine RPM information, fuel information, and the like.

Also, information related to the vehicle that can be displayed on the display unit 370 of the second main body can include brake pad warning information, washer liquid/air pressure warning information, anti-lock brake system (ABS) warning information, manual brake warning information, electronic stability program (ESP) warning information, collision possibility notification information, and the like.

That is, the processor 382 of the second main body can be attached to one mode of the vehicle to sense a state of the vehicle, and control the display unit 370 to output different screen information according to a state of the vehicle. In other words, different screen information can be output on the display unit 370 of the second main body according to a state of the vehicle.

Also, based on a preset type of touch (e.g., a short touch, a long touch, a drag touch, a swipe touch, a flick touch, and the like) applied to the display unit 370, the processor 382 of the second main body can change information related to the vehicle output on the display unit 370. In addition, even though the second main body is provided in the vehicle, when the first main body is present within a predetermined distance from the second main body (e.g., when the user who wears the first main body drives the vehicle or rides together), the controller 180 of the first main body can continuously sense a state of the user by using the sensing unit 140 provided in the first main body.

Thereafter, when a state of the user corresponds to a preset state (e.g., when a fatigue value is equal to or higher than a predetermined level or in case of an emergency (e.g., a heart attack)), the controller 180 of the first main body can control the second main body to perform a function associated to be performed in the preset state.

Based on a control command of the first main body, the second main body can perform the associated function and output information related to the function on the display unit 370. In addition, when a position of the vehicle to which the second main body is attached is changed, the processor 382 can control the display unit to change information related to the vehicle output on the display unit 370 provided in the second main body.

The vehicle can have at least one position to which the second main body can be attached. For example, when the second main body separated from the first main body is attached to a first position (e.g., a wind shield) of the vehicle, the processor 382 can control the sensing unit 140 to sense first information (e.g., weather information, surrounding brightness, an object near the vehicle, etc.).

In another example, when the second main body is attached to a second position (e.g., near a cluster) different from the first position, the processor 382 can control the sensing unit 140 to sense second information (e.g., information related to driving of the vehicle, such as a vehicle speed, an amount of lubrication, and the like) different from the first information.

The present invention described above can be implemented as a computer-readable code in a medium in which a program is recorded. The computer-readable medium includes any type of recording device in which data that can be read by a computer system is stored. The computer-readable medium can be, for example, a hard disk drive (HDD), a solid state disk (SSD), a silicon disk drive (SDD), a ROM, a RAM, a CD-ROM, a magnetic tape, a floppy disk, an optical data storage device, and the like. The computer-readable medium also includes implementations in the form of carrier waves (e.g., transmission via the Internet). Also, the computer can include the controller 180 of the terminal. Thus, the foregoing detailed description should not be interpreted limitedly in every aspect and should be considered to be illustrative. The scope of the present invention should be determined by reasonable interpretations of the attached claims and every modification within the equivalent range are included in the scope of the present invention.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein can be combined in various ways to obtain additional and/or alternative exemplary embodiments.

As the present features can be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. A watch type mobile terminal comprising:
a wrist band;
a main system including a circuit board for operating the watch type mobile terminal;
a main frame connected to the wrist band and encasing the main system;
a fob detachably connected to the main system; and
a display detachably connected to the fob,
wherein the fob includes:
a first connector configured to be connected to a connector of the main system when the fob is connected to the main system; and
a second connector configured to be connected to a connector of the display when the display is connected to the fob, and
wherein the connector of the display is configured to be connected to the connector of the main system when the fob is separated and the display is connected to the main system.

2. The watch type mobile terminal of claim 1, wherein each of the main system, the fob, and the display include a wireless communication unit, and
wherein when at least one of the fob and the display is separated, the separated at least one of the fob and the display perform wireless communication through the wireless communication unit.

3. The watch type mobile terminal of claim 1, wherein the fob and the display includes a connector configured to be connected to a connector of an external device.

4. The watch type mobile terminal of claim 3, wherein when the display is separated from the watch type mobile terminal and the connector of the display is connected to the connector of the external terminal, the watch type mobile terminal senses information related to the watch type mobile terminal, transmits the sensed information to the display connected to the external terminal, and at least one of the display connected to the external display and a touch screen of the external terminal displays information based on the transmitted sensed information.

5. The watch type mobile terminal of claim 4, wherein the sensed information corresponds to information sensed about a user wearing the watch type mobile terminal.

6. The watch type mobile terminal of claim 1, wherein when the display is separated from the watch type mobile terminal and is connected to an external device, screen information related to the external device is displayed on the display.

7. The watch type mobile terminal of claim 1, wherein the watch type mobile terminal is operable in at least one of
a first type in which the main system, the fob, and the display are all coupled,
a second type in which the main system and the fob are coupled and the display is separated from the fob,
a third type in which the fob and the display are coupled and the fob is separated from the main system, and
a fourth type in which all the main system, the fob, and the display are separated.

8. A method of controlling a watch type mobile terminal including a wrist band; a main system including a circuit board for operating the watch type mobile terminal; a main frame connected to the wrist band and encasing the main system; a fob detachably connected to the main system; and a display detachably connected to the fob, the control method comprising:
sensing that the display unit is separated from the fob;
sensing information through a sensor provided in the watch type mobile terminal when the separated display is attached to the external terminal; and
displaying information related to the sensed information on at least one of the display and a touch screen of the external terminal,
wherein the fob includes:
a first connector configured to be connected to a connector of the main system when the fob is connected to the main system; and
a second connector configured to be connected to a connector of the display when the display is connected to the fob, and
wherein the connector of the display is configured to be connected to the connector of the main system when the fob is separated and the display is connected to the main system.

9. The method of claim 8, wherein each of the main system, the fob, and the display include a wireless communication unit, and
wherein when at least one of the fob and the display is separated, the separated at least one of the fob and the display perform wireless communication through the wireless communication unit.

10. The method of claim 8, wherein the fob and the display includes a connector configured to be connected to a connector of an external device.

* * * * *